US005800997A

United States Patent [19]

Beck

[11] Patent Number: 5,800,997
[45] Date of Patent: Sep. 1, 1998

[54] DETECTION OF MAIZE FUNGAL PATHOGENS USING THE POLYMERASE CHAIN REACTION

[75] Inventor: James Joseph Beck, Cary, N.C.

[73] Assignee: Novartis Finance Corporation, New York, N.Y.

[21] Appl. No.: 742,023

[22] Filed: Nov. 1, 1996

[51] Int. Cl.$^6$ .............................. C12Q 1/68; C12P 19/34; C07H 21/04
[52] U.S. Cl. ........................ 435/6; 435/91.2; 435/91.3; 536/23.1; 536/24.1; 536/24.2; 536/24.3; 536/24.33; 935/6; 935/17; 935/77; 935/78
[58] Field of Search .................... 435/4, 6, 91.2, 435/91.5, 810; 536/23.1, 24.1–24.33, 24.3; 935/6–8, 17, 77, 78

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,324,632 | 6/1994 | Weisburg et al. | 435/6 |
| 5,447,848 | 9/1995 | Barns | 435/29 |
| 5,585,238 | 12/1996 | Ligon et al. | 435/6 |

FOREIGN PATENT DOCUMENTS

| | | |
|---|---|---|
| WO 91/14001 | 9/1991 | WIPO . |
| WO 95/24260 | 11/1995 | WIPO . |

OTHER PUBLICATIONS

Olivier et al. Phytopathology vol. 86 No. 11, Supplement pp. S1 and S12, Nov. 1996.
Bentolila et. al. Theoret. Appl. Genet 82:393–8 (Sep. 1991).
Olivier et. al. Phytopathology 86(11):812 (Nov. 1996).
Johanson et al. Use of PCR for detection of *Mycosphaerella fijiensis* and *M. musicola*", the causal agents of Sigatoka leaf spots in banana and plantain", *Mycol. Res.*, 97:670–674 (1993).
Nazar, R.N., et al, "Potential use of PCR-amplified ribosomal intergenic sequences in the detection and differentiation of verticillium wilt pathogens", *Physiol. and Molec. Plant Pathol.*, 39:1–11 (1991).
Poupard et al., "Molecular characterization of *Pseudocercosporella herpotrichoides* isolates by amplification of ribosomal DNA internal transcribed spaces", *Plant Pathology*, 42: 873–881 (1993).
Schesser et al., "Use of Polymerase Chain Reaction To Detect the Take–All Fungus, *Gaeumannomyces graminis*, in Infected Wheat Plants", *Applied and Environ. Microbiol.*, 57(2):553–556 (1991).
Stratagene Catalog, 1988, p. 39.
Tisserat et al., "Selective Amplification of rDNA Internal Transcribed Spacer Regions to Detect *Ophiosphaerella korrae* and *O. herpotricha*", *Phytopathology*, 84(5): 478–482 (1994).
White, T.J., et al., "Amplification and Direct Sequencing of Fungal Ribosomal RNA Genes for Phylogenetics", In: *PCR Protocols*; Academic Press Inc., pp. 315–322 (1990).
GenBank Accession No. L08734, computer printout, Feb. 5, 1993.
Xue et al., "Pathotype identification of *Leptosphaeria maculans* with PCR and oligonucleotide primers from ribosomal internal transcribed spacer sequences", *Physiological and Molecular Plant Pathology*, 41: 179–188 (1992).

Primary Examiner—W. Gary Jones
Assistant Examiner—Debra Shoemaker
Attorney, Agent, or Firm—J. Timothy Meigs

[57] ABSTRACT

Internal Transcribed Spacer (ITS) DNA sequences from the ribosomal RNA gene region are described for different species and strains of *Helminthosporium carbonum*, *Helminthosporium turcicum*, *Helminthosporium maydis*, *Cercospora zeae-maydis*, *Kabatiella zeae* and *Puccinia sorghi*. Specific primers from within these sequences are identified as being useful for the identification of the fungal isolates using PCR-based techniques.

38 Claims, 13 Drawing Sheets

```
                     10         20         30         40         50         60
                      |          |          |          |          |          |
Czeae-maydis    CCTA~~CCGTAGGTGAAC~CTGC~GGAGGGATCATTACTGAGTGAGGGCCT~~TCGGGCT   54
Hmaydis.con     C~~~TTTCCTAGGAGAAC~CTGC~KGAGGGATCATTACACAAC~~MAAAYAYG~AAGGYC   52
Hcarb.con       CCTTMTCCTAGGAGAAC~CTGC~GGAGGGATCATTACACAAC~~CAAATAWG~AAGGCC    55
Hturcicum1.co   G~~~TTCCCTAGGAGMAC~CTGCTGGAGGAYCATTACACAAGAYAYGRAGGTAGGGTA     56
Hturcicum2.co   ~~~~~TCCGTAGGAGAMCTCTGMTGGAGGGATCATTACMCAAAGAYAYGRAGGTAGGGTA   55

70         80         90        100        110        120
                      |          |          |          |          |          |
Czeae-maydis    C~GACCTCCAACCCTTTGTGAACACAACTWGTTGCTTCGGGG~~~~GCGACCCTGCCGT    108
Hmaydis.con     ~TGGC~~WTTKCGGCCGGYTGWAATAYTTTTTTCACCCAWGTCYTTTGCGCACTWGTWGT    109
Hcarb.con       CTGGC~~TTCGCGGCCGGCTGAAATATTTTT~CACCCATGTCTTTTGCCGCACTGTTGT     112
Hturcicum1.co   CTGGCAW~CAGTGCTCTGCTGAAATATTTT~~~CACCCAWGTCTTTTGCGCACTTTTDGT    112
Hturcicum2.co   CTGGCAATCAGTGCTCTCTKCTGAAATATTTT~~~CACCCAWGTCTTTWGCCGCACTTTTWGT 112

130        140        150        160        170        180
                      |          |          |          |          |          |
Czeae-maydis    TCCGACGGCGAG~~~~~~~CGCCCCGGAGGCC~~TTCAAACACTGCATCTT~TGCG~~~    155
Hmaydis.con     WTCCTGGGCGGGTWCGCCCGCCGCCACCAGGACCAAACCATAAACCATTTTTTTT~ATGCAGTT 169
Hcarb.con       TTCCTGGGCGGGTTGCCCGCCACCAGGACCAGGACCAAACCATAAACCTTTTTTTTATGCAGTT 172
Hturcicum1.co   TTCCTGGKCGAGTTWGCWCKCCACCAGGACCCCCATAWGAACCTTTTYGTTTTK~~~~~      167
Hturcicum2.co   WTCCTGGKCGAGTTYGCWCKCCACCAGGACCCCCATAYGAACCTTTTTYGTTTY~~~~       167

190        200        210        220        230        240
                      |          |          |          |          |          |
Czeae-maydis    ~~~~TCGG~~~~AGTTTAAGTAA~~~~ATTAAACAAAACTTTCAACA~~ACGGATCTCTT     201
Hmaydis.con     GCAATCAGCGTCAGTATAAACAABGTAATTA~TTACAACTTTCA~CMCAACGGATCTCTT     227
Hcarb.con       ACCATCAGCGTCAGTAAAAACAATGTAATTAATTACAACTTTCA~ACAACGGATCTCTT     230
Hturcicum1.co   GCACTCAGCGTCAGKACAA~TAATTDAADCTATTAAAACTTTCAACMCAACGGATCTCTT    226
Hturcicum2.co   GCACWCAGCGWCAGTACAA~TAATTAATCTATTMAAACTTTCA~CMCAACGGATCTCKT    225
```

FIGURE 1A

```
              250        260        270        280        290        300
               |          |          |          |          |          |
Czeae-maydis   GGTTCTGGCATCGATGAAGAACGCAGCGAAATGCGATAAGTAATGTGAATTGCAGAATTC 261
Hmaydis.con    GGTTCTGGMATCGATGAAGAACGCAGCGAAATGCGATAAGTAATGTGAATTGCAGAATTC 287
Hcarb.con      GGTTCTGGCATCGATGAAGAACGCAGCGAAATGCGATACGTRGTGTGAATTGCAGAATTC 290
Hturcicum1.co  GGTTCTGGCATCGATGAAGAACKCASCGAAATGCGATACGTAGTGTGAATTGCAGAATTC 286
Hturcicum2.co  GGTTCTGGCATCGATGAAGAACKCASCGAAATGCGATACGTAGTGTGAATTGCAGAATTC 285

310        320        330        340        350        360
               |          |          |          |          |          |
Czeae-maydis   AGTGAATCATCGAATCTTTGAACGCATATTGCGCCCTTTGGTATTCCGAAGGGCATGCCT 321
Hmaydis.con    AGTGAATCATCGAATCTTTGAACGCACATTGCGCCCTTTGGTATTCCAAAGGGCATGCCT 347
Hcarb.con      AGTGAATCATCGAATCTTTGAACGCACATTGCGCCCTTTGGTATTCCAAAGGGCATGCCT 350
Hturcicum1.co  AGTGAATCATCGAATCTTTGAACGCACATTGCGCCCTTTGGTATTCCAAAGGGCATGCCT 346
Hturcicum2.co  AGTGAATCATCGAATCTTTGAACGCACATTGCGCCCTTTGGTATTCCAAAGGGCATGCCT 345

370        380        390        400        410        420
               |          |          |          |          |          |
Czeae-maydis   GTTCGAGCGTCATTT~CACCACTCAAGCTTGGTATTGGGCGCCGGTGTTCC~~ 378
Hmaydis.con    GTTCGAGCGTCATTWGTA~CCCTCAAGCTTTGCTTGGTCGTTTKGTCTCCCTC 406
Hcarb.con      GTTCGAGCGTCATTTGTA~CCTTCAAGCTTTGYTTGGTGTTGGCGTTTKGTCTCCCTC 409
Hturcicum1.co  GTTCGAGCGTCATKTGKDACCCTCAAGCTTTGCTTGGYGTTGGGCGTCTTATTGTCTCTC 406
Hturcicum2.co  GTTCGAGCGTCATTTGKA~CCCTCAAGCTTTGCTTGGBGTTGGGCGTCTTATTGTCTCTC 404

430        440        450        460        470        480
               |          |          |          |          |          |
Czeae-maydis   ~~~~~~~GCGCGCCTTAAAG~~~TCTCCGGCTGAGCTGTCCGTCTCTAAGCGTNG 423
Hmaydis.con    TTTRCTGGG~AGACTCGCCTTAAAACGATTGGCAGCCGCCTACTGGTTCGAGCGCAG 465
Hcarb.con      TTTC~TGGG~AGACTCGCCTTAAAACGATTGGMAGCCGCCTACTGGTTCGAGCGMAG 467
Hturcicum1.co  CGYCTCGGGGAGACTCGCCTTAAAACAATTGGCAGCCGCCTACTGGTTCGGAGCGCAG 466
Hturcicum2.co  CGYCTCGGGGAGACTCGCCTTAAAACAATTGGCAGCCGCCTACTGGTTCGRAGCGCAG 464
```

FIGURE 1B

|  | 490 | 500 | 510 | 520 | 530 | 540 |  |
|---|---|---|---|---|---|---|---|
| Czeae-maydis | TG-ATTTCAT~TAATCGCTTCGGAGCGCGGGGCGGTTCGCGGCCGTCTAAATCTTTCACAAG | | | | | | 481 |
| Hmaydis.con | CACATATTTTGCACTCNGTATCAGGAGAGAAAAGGVCGGTAATCCATCAAGACTCTTACGAT | | | | | | 525 |
| Hcarb.con | CACATAATTTGCGCTTHGTATCAGGAGAGAAAAGGACGGTAATCCATCAAGACTCT-A-GAT | | | | | | 525 |
| Hturcicum1.co | CACA-AATTWGCGCTWGCAATCAGCC~~~AAGGGCGGSA~TCCAWGAAGCCTYTWTT~~C | | | | | | 519 |
| Hturcicum2.co | CACA-AATTWGCGCTKGCAATCAGCC~~~AAGGGCGGSA~TCCAWGAAGCCTTTTTW~~C | | | | | | 517 |

|  | 550 | 560 | 570 | 580 | 590 | 600 |  |
|---|---|---|---|---|---|---|---|
| Czeae-maydis | G~~~~~~TTGACCTCGGATCAGGTAGGGATACCCGYTGAACKTAAGATATATCACTA | | | | | | 532 |
| Hmaydis.con | TTTKAACTTTNGACCTCGGAWCAGGWAGKGATACCCGCTGAACTTAAG-CATATCACTAA | | | | | | 584 |
| Hcarb.con | TTTTAACTTTDGACCTCGGATCAGGTAGGGRTACCCGCTGAACKTAAG-CATATCA | | | | | | 580 |
| Hturcicum1.co | TCTCACATTTYGACCTCGGAWCAGGWAGGGATACCCGCTGAACKTAAG-CATATCACTA | | | | | | 577 |
| Hturcicum2.co | TCTCACATTTTGACCTCGGAWCAGGWAGGGATACCCGCTGAACGT | | | | | | 562 |

|  | 610 |  |
|---|---|---|
| Czeae-maydis |  | 532 |
| Hmaydis.con | GCGAGGGAAG | 594 |
| Hcarb.con |  | 580 |
| Hturcicum1.co |  | 577 |
| Hturcicum2.co |  | 562 |

FIGURE 1C

```
                        10         20         30         40         50         60
                        |          |          |          |          |          |
KZ18594.CON    T----AGGTGAACCTGCGGAAGGAWCWTTAAAGAGTARGGGTGCCCAGCGCCCGACCTCC        56
KZ5125.CON     ..........AGGTGAACCTGCGGAAGGAWCWTTAAAGAGTA-------AGCGCCCGACCTCC        14
KZ56351(5-1)   TCCGTAGGTGAACCTGCGGAAGGATCATTAAAGAGTA-------AGGGTGCCCAGCGCCCGACCTCC  60

70         80         90        100        110        120
                        |          |          |          |          |          |
KZ18594.CON    AACCCTTTGTTGTTAAAACTACCTTGTTGCTTTGGCGGGGACCCGCTCGGTCCCCCGAGCCGC       116
KZ5125.CON     AACCCTTWTGTTGTTAAAACTACSTTGTTGCTTTGGCGGGGACCCGCTCGGTCCCCCGAGCCGC       74
KZ56351(5-1)   AACCCTTTGTTGTTAAAACTACCTTGTTGCTTTGGCGGGGACCCGCTCGGTCCCCCGAGCCGC       120

130        140        150        160        170        180
                        |          |          |          |          |          |
KZ18594.CON    CGGGGGATCCGTCCCCCATGGGCGGAGCGCCCGCCGGGAGTTAAACCAAACTCTTGTTGAAC        176
KZ5125.CON     MGGGGGATCCGTCCCCCATGGGCGGAGCGCCCGCCGGGAGTTAAACCAAACTCTTGTTGAAC        134
KZ56351(5-1)   CGGGGGATCCGTCCCCCATGGGCGGAGCGCCCGCCGGGAGTTAAACCAAACTCTTGTTGAAC        180

190        200        210        220        230        240
                        |          |          |          |          |          |
KZ18594.CON    AAACCGGTCGTCTGAGTTAAAATTTTGAATAAAATCAAAACTWTCWACAACGGATCTCTTG        236
KZ5125.CON     AAACCGGTCGTCTGAGTTAAAATTTTGAATAAAATCAAAACTTTCAACAACGGATCTCTTG        194
KZ56351(5-1)   AAACCGGTCGTCTGAGTTAAAATTTTGAATAAAATCAAAACTTTCAACAACGGATCTCTTG        240

250        260        270        280        290        300
                        |          |          |          |          |          |
KZ18594.CON    GTTSTCGCATCGATGAAGAACGCAGCGAAMTGCGATAAGTAATGTGAATTGCAGAATTCA         296
KZ5125.CON     GTTCTCGCATCGATGAAGAACGCAGCGAAATGCGATAAGTAATGTGAATTGCAS AATTCA         254
KZ56351(5-1)   GTTCTCGCATCGATGAAGAACGCAGCGAAATGCGATAAGTAATGTGAATTGCAGAATTCA         300

310        320        330        340        350        360
                        |          |          |          |          |          |
KZ18594.CON    GTGAATCATCGAATCTTTGAACGCACATTGCGCCCCTTGGTATTCCGAGGGGCATGCCTG         356
KZ5125.CON     GTGAATCATCGAATCTTTGAACGCACATTGCGCCCCTTGGTATTCCGAGGGGCATGCCTG         314
KZ56351(5-1)   GTGAATCATCGAATCTTTGAACGCACATTGCGCCCCTTGGTATTCCGAGGGGCATGCCTG         360
```

FIGURE 2A

```
                        370        380        390        400        410        420
                        |          |          |          |          |          |
KZ18594.CON  TTCGAGCGTCATTACACCACTCAAGCTCTGCTTTGGTATTGGGCGTCCGTCCTTTCGGGGG  416
KZ5125.CON   TTCGAGCGTCATTACACCACTCHAGCTCTGCTTGGTATTGGGCGTCCGTCCTTTCGGGGG  374
KZ56351(5-1) TTCGAGCGTCATTACACCACTCAAGCTCTGCTTGGTATTGGGCGTCCGTCCTTTCGGGGG  420

430        440        450        460        470        480
                        |          |          |          |          |          |
KZ18594.CON  CGCGCCTCAAACACCTCGGMGARGCCTCACCGGYTTCAGGCGTAGTADAATTCATTCAAT  476
KZ5125.CON   CGCGCCTCAAACACCTCGGMGAGGCCTCACCGGYTTCAGGCGTAGTAGAATTCATTCAAT  434
KZ56351(5-1) CGCGCCTCAAACACCTCGGCGAGGCCTCACCGGCTTCAGGCGTAGTAGAATTCATTCAAT  480

490        500        510        520        530        540
                        |          |          |          |          |          |
KZ18594.CON  CAACGTCTGGCGAAACCGGAGGGGACTTCTGCCGACAGAAACCTTTATATTTTCTAGGT  536
KZ5125.CON   CAACGTCTGGCGAAACCGGAGGGGACTTCTGCCGACAGAAACCTTTTTAWATTTTCTARGT  494
KZ56351(5-1) CAACGTCTGGCGAAACCGGAGGGGACTTCTGCCGACAGAAACCTTTTATATTTTCTAGGT  540

550        560        570        580        590
                        |          |          |          |          |
KZ18594.CON  TGACCTCGGATCAGGTAGGGATACCCGCTGAACTTAAGCATATCA                 581
KZ5125.CON   TGACCTCGGATCAGGTAGGGATACCCGCTGAACTTAAGCATATCAATAAC------A    545
KZ56351(5-1) TGACCTCGGATCAGGTAGGGATACCCGCTGAACTTAAGCATATCAATAAGCGGAGGA    597
```

Block 1 (positions 1-60):
```
                              10        20        30        40        50        60
HM11534(4-1)  TCCGTAGGTGAACCTGCGCGGAGGGATCATTACACAACAACAAAATATGAAGGCCTGGCTTTGCG   60
HM11534.CON   T.........................ACACAACAACAAAATATAWGAAGGCCTGGCTTTGCG    32
HM24772(2-1)  TCCGTAGGTGAACCTGCGCGGAGGGATCATTACACAACAACAAAATATGAAGGCCTGGCTTTGCG   60
HM6921.CON    ....TAGGAGAACCTGCKGAGGGATCATTACACAACAACMAAYAYGAAGGYCTGGCWTTKCG    56
```

Block 2 (positions 61-120):
```
                              70        80        90       100       110       120
HM11534(4-1)  GCCGGCTGAAATATTTTTTCACCCCATGTCTTTTGCGCACTTGTTGTTTCCTGGGCGGGGT   120
HM11534.CON   GCCGGCTGAAATATTTTTTCACCCCATGTCTTTTGCGCACTTGTTGTTTCCTGGGCGGGGT   92
HM24772(2-1)  GCCGGCTGAAATATTTTTTCACCCCATGTCTTTTGCGCACTTGTTGTTTCCTGGGCGGGGT   120
HM6921.CON    GCCGGYTGWAATAYTTTTTTCACCCCAWGTCYTTTGCGCACTWGTWGTWTCCTGGGCGGGT    116
```

Block 3 (positions 121-180):
```
                             130       140       150       160       170       180
HM11534(4-1)  TCGCCCGCCACCAGGACCAAACCATAAACCTTTTTTTTTTATGCAGTTGCAATCAGCGTCAG   180
HM11534.CON   TCGCCCGCCACCAGGACCAAACCATAAACCTTTTTTTTTTATGCAGTTGCAATCAGCGTCAG   152
HM24772(2-1)  TCGCCCGCCACCAGGACCAAACCATAAACCCTAAACCTTTTTTTTTATGCAGTTGCAWTCAGCGTCAG   180
HM6921.CON    WCGCCCGCCACCAGGACCAAACCATAAACCTTTTTTTTTATGCAGTTGCAATCAGCGTCAG   176
```

Block 4 (positions 181-240):
```
                             190       200       210       220       230       240
HM11534(4-1)  TATAAACAATGTAATTATTATTACAACTTTCA-ACAACGGATCTCTTGGTTCTGGCATCGATG   239
HM11534.CON   TATAAACAATGTAATTATTATTACAACTTTCA-ACAACGGATCTCTTGGTTCTGGCATCGATG   211
HM24772(2-1)  TATAAACAATGTAATTATTATTACAACTTTCA-ACAACGGATCTCTTGGTTCTGGCATCGATG   239
HM6921.CON    TATAAACAABGTAATTATTACAACTTTCACMCAACGGATCTCTTGGTTCTGGMATCGATG      236
```

Block 5 (positions 241-300):
```
                             250       260       270       280       290       300
HM11534(4-1)  AAGAACGCAGCAGCGAAATGCGATACGTAGTAGTGAATTGCAGAATTCAGTGAATCATCGAATC   299
HM11534.CON   AAGAACGCAGCAGCGAAATGCGATACGTAGTAGTGAATTGCAGAATTCAGTGAATCATCGAATC   271
HM24772(2-1)  AAGAACGCAGCAGCGAAATGCGATACGTAGTAGTGAATTGCAGAATTCAGTGAATCATCGAATC   299
HM6921.CON    AAGAACGCAGCAGCGAAATGCGATACGTRGTGTGAATTGCAGAATTCAGTGAATCATCGAATC    296
```

FIGURE 3B

```
Htur26306.con   TCCGTAGGTGAACCTGC- GGAGGGATCATTACCAAAGATATGAAGGTAGGGTACTGGCA    59
Htur6586.con    ...-TAGGAGAGAACCCTGCTGCTGMTGGAGGGATCATTACCAAAGAYAYGRAGGTAGGGTACTGGCA  56
Htur6402.con    TCCGTAGGAGAACCTGCTGMTGGAGGGATCATTACCAAAGAYAYGRAGGTAGGGTACTGGCA         60
HT26306(3-1)    TCCGTAGGTGAACCTGC- GGAGGGATCATTACACAAAGATATGAAGGTAGGGTACTGGCA          59

Htur26306.con   ACAGTGCTCTGCTGAAATATTTTCACCCCATGTCTTTTGCGCACTTTTTGTTTCCTGGGCG    119
Htur6586.con    WCAGTGCTCTGCTGCTGAAATATTTTCACCCCAWGTCTTTTGCGCACTTTTTDGTTTCCTGGKCG     116
Htur6402.con    ACAGTGCTCTGCTKCTGAAATATTTTCACCCCAWGTCTTTTWGCGCACTTTTTWGTWTCCTGGKCG    120
HT26306(3-1)    ACAGTGCTCTGCTGAAATATTTTCACCCCATGTCTTTTTGCGCACTTTTTGTTTCCTGGGCG        119

Htur26306.con   AGTTTGCTCGCCACCAGGACCCCCCATATGAACCTTTTTTTTGTTTTTGCACTCAGCGTCAGT       179
Htur6586.con    AGTTTWGCWCWCCACCAGGACCCCCCATAWGAACCTTTTTTTTYGTTTTTKGCACTCAGCGTCAGK    176
Htur6402.con    AGTTTYGCWCTCGCCACCAGGACCCCCCATAYGAACCTTTTTTTTTYGTTTTYGCACWCAGCGWCAGT 180
HT26306(3-1)    AGTTTGCTCGCCACCAGGACCCCCCATATGAACCTTTTTTTTGTTTTTGCACTCAGCGTCAGT       179

Htur26306.con   ACAATAATTTAATCTATTAAAACTTTCA- ACAACGGATCTCTTGGTTCTCTGGCATCGATGA       238
Htur6586.con    ACAATAATTDAADCTATTAAAACTTTTCAMCCAACGGATCTCTTGGTTCTCTGGCATCGATGA       236
Htur6402.con    ACAATAATTTAATCTATTMAAACTTTCACMCAACGGATCTCKTGGTTCTCTGGCATCGATGA        240
HT26306(3-1)    ACAATAATTTAATCTATTAAAACTTTCA- ACAACGGATCTCTTGGTTCTCTGGCATCGATGA       238

Htur26306.con   AGAACGCAGCGAAATGCGATACGTAGTGTGTAGTGCAGAATTCAGTGAATCATCGAATCT          298
Htur6586.con    AGAACKCASCGAAATGCGATACGTAGTGTGTAGTGCAGAATTCAGTGAATCATCGAATCT          296
Htur6402.con    AGAACKCASCGAAATGCGATACGTAGTGTGTAGTGCAGAATTCAGTGAATCATCGAATCT          300
HT26306(3-1)    AGAACGCAGCGAAATGCGATACGTAGTGTGTAGTGCAGAATTCAGTGAATCATCGAATCT          298
```

FIGURE 4A

```
                     310             320             330             340             350          360
Htur26306.con  TTGAACGCACATTGCGCCCTTTGGTATTCCAAAGGGCATGCCTGTTCGAGCGTCATTTGT  358
Htur6586.con   TTGAACGCACATTGCGCCCTTTGGTATTCCAAAGGGCATGCCTGTTCGAGCGTCATKTGK  356
Htur6402.con   TTGAACGCACATTGCGCCCTTTGGTATTCCAAAGGGCATGCCTGTTCGAGCGTCATTTGK  360
HT26306(3-1)   TTGAACGCACATTGCGCCCTTTGGTATTCCAAAGGGCATGCCTGTTCGAGCGTCATTTGT  358

370             380             390             400             410          420
Htur26306.con  A-CCCTCAAGCTTTGCTTGGTGTTGGGCGTCTTATTGTCTCTCCGTCTCGGGGAGACTCG  417
Htur6586.con   NACCCTCAAGCTTTGCTTGGYGTTGGGCGTCTTATTGTCTCTCCGYCTCGGGGAGACTCG  416
Htur6402.con   A-CCCTCAAGCTTTGCTTGGBGTTGGGCGTCTTATTGTCTCTCCGYCTCGGGGAGACTCG  419
HT26306(3-1)   A-CCCTCAAGCTTTGCTTGGTGTTGGGCGTCTTATTGTCTCTCCGTCTCGGGGAGACTCG  417

430             440             450             460             470          480
Htur26306.con  CCTTAAAACAATTGGCAGCCGGCCTACTGGTTTCGGAGCGCAGCACAAATTTGCGCTTGC  477
Htur6586.con   CCTTAAAACAATTGGCAGCCGGCCTACTGGTTTCGGAGCGCAGCACAAATTWGCGCTWGC  476
Htur6402.con   CCTTAAAACAATTGGCAGCCGGCCTACTGGTTTCGRAGCGCAGCACAAATTWGCGCTKGC  479
HT26306(3-1)   CCTTAAAACAATTGGCAGCCGGCCTACTGGTTTCGGAGCGCAGCACAAATTTGCGCTTGC  477

490             500             510             520             530          540
Htur26306.con  AATCAGCCAAGGGCGGCATCCATGAAGCCTTTTTCTCTCACATTTTGACCTCGGATCAG   537
Htur6586.con   AATCAGCCAAGGGCGGS ATCCAWGAAGCCTYTWTTCTCTCACATTTYGACCTCGGAWCAG  536
Htur6402.con   AATCAGCCAAGGGCGGS ATCCAWGAAGCCTTTTTWCTCTCACATTTTGACCTCGGAWCAG  539
HT26306(3-1)   AATCAGCCAAGGGCGGCATCCATGAAGCCTTTTTCTCTCACATTTTGACCTCGGATCAG   537

550             560             570           580
Htur26306.con  GTAGGGATACCCCGCTGAACTTAAGCATATCAATAAG                         573
Htur6586.con   GWAGGGATACCCCGCTGAACKTAAGCATATCA                              567
Htur6402.con   GWAGGGATACCCCGCTGAAC                                          558
HT26306(3-1)   GTAGGGATACCCCGCTGAACTTAAGCATATCAATAAGCGGAGGA                  580
```

```
                              370                380                390                400                410              420
CZM5860.CON  GCGCCGCGGTGTTCCGCGCGGCCCTTAAAGTCTCCGGCTGAGCTGTGTCCGTCTCTAAGCGTNG  419
CZMPOS12(2-1 GCGCCGCGGTGTTCCGCGCGGCCCTTAAAGTCTCCGGCTGAGCTGTGTCCGTCTCTAAGCGTTG  420
CZlad3-1(4-3) GCGCCGCGGTGTTCCGCGCGGCCCTTAAAGTCTCCGGCTGAGCTGTGTCCGTCTCTAAGCGTTG  419

430                440                450                460                470              480
CZM5860.CON  TGATTTCATTAATCGCTTCGGAGCCGCGGTCGCGGGCCGTCTAAATCTTTCACAAGGT  479
CZMPOS12(2-1 TGATTTCATTAATCGCTTCGGAGCCGCGGTCGCGGGCCGT-TAAATCTTTCACAAGGT  479
CZlad3-1(4-3) TGATTTCATTAATCGCTTCGGAGCCGCGGTCGCGGGCCGT-TAAATCTTTCACAAGGT  478

490                500                510                520                530
CZM5860.CON  TGACCTTCGGATCAGGTAGGGATACCCGYTGAACKTAAGATATATCACTA             528
CZMPOS12(2-1 TGACCTTCGGATCAGGTAGGGATACCCGCTGTACTTAAG-CATATCAATAAGCGGAGGA    536
CZlad3-1(4-3) TGACCTTCGGATCAGGTAGGGATACCCGCTGAACTTAAG-CATATCAATAAGCGGAGGA    535
```

FIGURE 5B

```
Hcar16185.con    - - - - - GTGAACCTGCGGGAGGGATCATTACACAACAAATATGAAGGCCCTGGCTTCGC    53
Hcar5870.con     - - - - TAGGAGAACCTGCGGGAGGGATCATTACACAACCAAATAWGAAGGCCCTGGCTTCGC    56
HC16185(5-2)     TCCGTAGGTGAACCTGCGGGAGGGATCATTACACAACAAATATGAAGGCCCTGGCTTCGC    60

Hcar16185.con    GGCCGGCTGAAATATTTTTCACCCATGTCTTTTGCGCACTTGTTGTTGTTCCTGGGCGGGT   113
Hcar5870.con     GGCCGGCTGAAATATTTTTCACCCATGTCTTTTGCGCACTTGTTGTTGTTCCTGGGCGGGT   116
HC16185(5-2)     GGCCGGCTGAAATATTTTTCACCCATGTCTTTTGCGCACTTGTTGTTGTTCCTGGGCGGGT   120

Hcar16185.con    TTGCCCGCCACCAGGACCAAACCATAAAACCTTTTTTTTTTATGCAGTTACCATCAGCGTCA   173
Hcar5870.con     TTGCCCGCCACCAGGACCAAACCATAAAACCTTTTTTTTTTTATGCAGTTACCATCAGCGTCA   176
HC16185(5-2)     TTGCCCGCCACCAGGACCAAACCATAAAACCTTTTTTTTTTTATGCAGTTACCATCAGCGTCA   180

Hcar16185.con    GTAAAAACAATGTAATTAATTACAACTTTCAACAACGGATCTCTTGGTTCTGGCATCGAT   233
Hcar5870.con     GTAAAAACAATGTAATTAATTACAACTTTCAACAACGGATCTCTTGGTTCTGGCATCGAT   236
HC16185(5-2)     GTAAAAACAATGTAATTAATTACAACTTTCAACAACGGATCTCTTGGTTCTGGCATCGAT   240

Hcar16185.con    GAAGAACGCAGCAGCGAAATGCGATACGTAGTGTGAATTCAGTGAATCATCGAAT   293
Hcar5870.con     GAAGAACGCAGCAGCGAAATGCGATACGTAGTGTGAATTCAGTGAATCATCGAAT   296
HC16185(5-2)     GAAGAACGCAGCAGCGAAATGCGATACGTAGTGTGAATTCAGTGAATCATCGAAT   300

Hcar16185.con    CTTTGAACGCACATTGCGCCCCTTTGGTATTCCAAAGGGCATGCCTGTTCGAGCGTCATTT   353
Hcar5870.con     CTTTGAACGCACATTGCGCCCCTTTGGTATTCCAAAGGGCATGCCTGTTCGAGCGTCATTT   356
HC16185(5-2)     CTTTGAACGCACATTGCGCCCCTTTGGTATTCCAAAGGGCATGCCTGTTCGAGCGTCATTT   360
```

FIGURE 6A

```
                              370         380         390         400         410         420
                              |           |           |           |           |           |
Hcar16185.con    GTACCTTCAAGCTTTGCTTGTGTGTTGGGCGTTTTTGTCTCCCTCTTTCTGGGAGACTCGC    413
Hcar5870.con     GTACCTTCAAGCTTTGYTTGTGCTTGGGGCGTTTTTKGTCTCCCTCTTTTCTGGGAGACTCGC   416
HC16185(5-2)     GTACCTTCAAGCTTTGCTTGTGTTGGGCGTTTTGTCTCCCTCTTTTCTGGGAGACTCGC       420

430         440         450         460         470         480
                              |           |           |           |           |           |
Hcar16185.con    CTTAAAACGATTGGCAGCCGGCCCTACTGGTTTCGGAGCGCAGCACATAATTTGCGCTTTG     473
Hcar5870.con     CTTAAAACGATTGGMAGCCGGCCCTACTGGTTTCGGAGCGCAGMAGCACATAATTTGCGCTTWG   476
HC16185(5-2)     CTTAAAACGATTGGCAGCCGGCCCTACTGGTTTCGGAGCGCAGCACATAATTTGCGCTTTG     480

490         500         510         520         530         540
                              |           |           |           |           |           |
Hcar16185.con    TATCAGGAGAAAAGGACGGTAATCCATCAAGACTCTAGATTTTTAACTTTTGACCTTCGGA     533
Hcar5870.con     TATCAGGAGAAAAGGACGGTAATCCATCAAGACTCTAGATTTTTAACTTTDGACCTTCGGA     536
HC16185(5-2)     TATCAGGAGAAAAGGACGGTAATCCATCAAGACTCTAGATTTTTAACTTTTGACCTTCGGA     540

550         560         570         580
                              |           |           |           |
Hcar16185.con    TCAGGTAGGGATACCCGCTGAACTTAAGCATATCAATAA                           572
Hcar5870.con     TCAGGTAGGGRTACCCGCTACCCGCTGAACKTAAGCATATCA                        571
HC16185(5-2)     TCAGGTAGGGATACCCGCTGAACTTAAGCATATCAATAAGCGGAGGA                   587
```

DETECTION OF MAIZE FUNGAL PATHOGENS USING THE POLYMERASE CHAIN REACTION

FIELD OF THE INVENTION

The present invention relates to the use of species-specific primers in polymerase chain reaction assays for the detection of fungal pathogens of maize. The use of these primers enables the detection of specific isolates of fungal pathogens and the monitoring of disease development in plant populations.

BACKGROUND OF THE INVENTION

Diseases in plants cause considerable crop loss from year to year resulting both in economic deprivation to farmers and, in many parts of the world, to shortfalls in the nutritional provision for local populations. The widespread use of fungicides has provided considerable security against plant pathogen attack. However, despite $1 billion worth of expenditure on fungicides, worldwide crop losses amounted to approximately 10% of crop value in 1981 (James, 1981; Seed Sci. & Technol. 9:679–685).

The severity of the destructive process of disease depends on the aggressiveness of the pathogen and the response of the host. One aim of most plant breeding programs is to increase the resistance of host plants to disease. Typically, different races of pathogens interact with different varieties of the same crop species differentially, and many sources of host resistance only protect against specific pathogen races. Furthermore, some pathogen races show early signs of disease symptoms, but cause little damage to the crop. Jones and Clifford (1983; Cereal Diseases, John Wiley) report that virulent forms of the pathogen are expected to emerge in the pathogen population in response to the introduction of resistance into host cultivars and that it is therefore necessary to monitor pathogen populations. In addition, there are several documented cases of the evolution of fungal strains that are resistant to particular fungicides. As early as 1981, Fletcher and Wolfe (1981; Proc. 1981 Brit. Crop Prot. Conf.) contended that 24% of the powdery mildew populations from spring barley and 53% from winter barley showed considerable variation in response to the fungicide triadimenol and that the distribution of these populations varied between varieties, with the most susceptible variety also giving the highest incidence of less susceptible types. Similar variation in the sensitivity of fungi to fungicides has been documented for wheat mildew (also to triadimenol), Botrytis (to benomyl), Pyrenophora (to organomercury), Pseudocercosporella (to MBC-type fungicides) and Mycosphaerella fijiensis to triazoles to mention just a few (Jones and Clifford; Cereal Diseases, John Wiley, 1983).

The three most important cereal crops in the world are maize (corn), rice and wheat (1973; Compendium of Corn Diseases, Amer. Phytopath. Soc. page 1). There are a great number of fungi, bacteria, and viruses that are pathogenic to maize, causing 9.4 % annual worldwide losses. In the corn belt of the United States, maize reduction because of disease infection is between 7 to 17% annually. Maize is the most important native American plant, and the U.S. produces about 44% of the world's 250 million metric tons annual production.

The major infectious diseases of maize are caused by fungi and include rusts, smuts, downy mildews, rots, spots, blights and deformations (1973; Compendium of Corn Diseases, Amer. Phytopath. Soc. page 13). Although fungal diseases are usually diagnosed by the structures produced by the pathogens, the differential symptomology caused by different isolates and species of these fungi make the accurate predictive determination of potential disease loss difficult. Consequently, the availability of improved diagnostic techniques for the rapid and accurate identification of specific pathogens will be of considerable use to field pathologists.

There are three primary species of Helminthosporium pathogenic to maize causing foliar diseases. *Helminthosporium carbonum* causes helminthosporium leaf spot (blight), also known as northern leaf spot (1973; Compendium of Corn Diseases, Amer. Phytopath. Soc. page 17). It is distributed throughout the Americas, southeast Asia, southeast Europe, south and central Africa, and India (Jones and Clifford; Cereal Diseases, John Wiley, 1983). There are two primary physiologically-based races. Race 1 is highly virulent on maize, causing a charred appearance on the ear's kernels. Race 2 tends to be less virulent than race 1 and does not diplay host specificity. Race 2 produces a host-specific toxin. *Helminthosporium maydis* causes southern leaf blight in maize. It occurs worldwide in warm (20°–32° C.), humid climates. In the United States, it is found in the southeastern and midwestern states (Jones and Clifford; Cereal Diseases, John Wiley, 1983). The disease was originally thought to be of little economic importance until a severe 1970 epidemic in the U.S. resulted in large losses. Northern leaf blight (turcicum leaf blight) is caused by *Helminthosporium turcicum*. The disease develops in humid areas of the world where maize is grown (1973; Compendium of Corn Diseases, Amer. Phytopath. Soc. page 16). Moderate temperatures (18°–27° C.) and heavy dews during the growing season promote severe disease development in which 50% losses of grain can occur. Typical control of these diseases include the use fungicides, crop rotation, burning crop debris, and breeding resistant hybrids and varieties.

*Kabateilla zeae* is another significant maize foliar pathogen causing eyespot disease. The disease originally reported as brown eyespot in Japan has also been found in Canada, Argentina, Austria, France, Germany, Yugoslavia, New Zealand and in several north-central U.S. states and Pennsylvania (1973; Compendium of Corn Diseases, Amer. Phytopath. Soc. page 21). The disease may develop on sheaths and outer husks, but lesions are more concentrated on leaves approaching maturity. In extremely infected plants, kernel infections may also develop. Cool, humid weather favors disease development. Disease control measures include the use of less susceptible hybrids, fungicides, and clean plowing or crop rotation.

Cercospora or gray leaf spot is caused by *Cercospora zeae-maydis* and infects maize, barnyardgrass, Johnsongrass and other Sorghum species (1973; Compendium of Corn Diseases, Amer. Phytopath. Soc. page 24). The disease is prevalent in warm-to-hot, humid areas of the United States, Mexico, Central America, northern South America, Europe, Africa, southeast Asia, India, China, and the Philippines. The disease has increased in severity in recent years in the southeastern and mid-Atlantic states of the U.S. especially in areas using minimum tillage of maize and no crop rotation (Latterell and Rossi, 1983; *Plant Disease*. Vol. 67, No. 8:842–847). The disease can spread from the leaf sheaths to the stalk in highly infected plants. This can cause stalk deterioration to the point where lodging precludes mechanical harvesting. Crop rotation, resistant cultivars and fungicides are currently used to control gray leaf spot.

*Puccinia sorghi* causes common maize rust and can be found wherever maize is grown. Infection can occur on any plant parts above ground but is mainly found on the leaves (1973; Compendium of Corn Diseases, Amer. Phytopath. Soc. page 24). Cooler temperatures (16°–23° C.) and high moisture contribute to the proliferation of the disease. Under severe infection conditions, chlorosis and death of the leaves and sheaths may occur ultimately reducing cereal yield.

Thus, there is a real need for the development of technology that will allow the identification of specific races of pathogen fungi early in the infection process. By identifying the specific race of a pathogen before disease symptoms become evident in the crop stand, the agriculturist can assess the likely effects of further development of the pathogen in the crop variety in which it has been identified and can choose an appropriate fungicide if such application is deemed necessary.

Additionally, with the increasing need for DNA fingerprinting, restriction fragment length polymorphism (RFLP) analysis, Southern transfers and PCR analysis, the isolation of high molecular weight DNA becomes a major problem when attempting to process a large number of plant samples in a timely manner. Several methods for the isolation of DNA have been reported, all of which have drawbacks for various reasons. These include DNA losses due to degradation and adsorption, the co-isolation of PCR inhibiting contaminants and labor extensive and costly protocols. Therefore, there is a need for a DNA extraction method which isolates high molecular weight DNA for high throughput analysis using molecular biology methods.

SUMMARY OF THE INVENTION

The present invention is drawn to methods of identification of different pathotypes of plant pathogenic fungi. The invention provides Internal Transcribed Spacer (ITS) DNA sequences that show variability between different fungal pathotypes. In a preferred embodiment, the invention provides ITS 1 and ITS2 DNA sequences for the pathogens *Helminthosporium carbonum*, *Helminthosporium turcicum*, *Helminthosporium maydis*, *Cercospora zeae-maydis*, *Kabatiella zeae*, and *Puccinia sorghi*. Such DNA sequences are useful in the method of the invention as they can be used to derive primers for use in polymerase chain reaction (PCR)-based diagnostic assays. These primers generate unique fragments in PCR reactions in which the DNA template is provided by specific fungal pathotypes and can thus be used to identify the presence or absence of specific pathotypes in host plant material before the onset of disease symptoms.

This invention provides the possibility of assessing potential damage in a specific crop variety-pathogen strain relationship and of utilizing judiciously the diverse armory of fungicides which is available. Furthermore, the invention can be used to provide detailed information on the development and spread of specific pathogen races over extended geographical areas. The invention provides a method of detection that is especially suitable for diseases with a long latent phase. In addition, a method is described for extracting DNA from plant tissue for high throughput PCR analysis.

Kits useful in the practice of the invention are also provided. The kits find particular use in the identification of the pathogens *Helminthosporium carbonum*, *Helminthosporium turcicum*, *Helminthosporium maydis*, *Cercospora zeae-maydis*, *Kabatiella zeae*, and *Puccinia sorghi*.

DESCRIPTION OF THE FIGURES

FIGS. 1A, 1B, and 1C Sequence Alignment of the ITS regions from *Cercospora zeae-maydis*, *Helminthosporium maydis*, *Helminthosporium carbonum*, and two isolates of *Helminthosporium turcicum*.

FIGS. 2A and 2B Sequence Alignment of the ITS regions from *Kabatiella zeae* isolates 18594 and 5125 and from clone pCRKZ56351(5-1).

FIGS. 3A and 3B Sequence Alignment of the ITS regions from clone pCRHMAY11534(4-1), from *Helminthosporium maydis* isolate 11534, from clone pCRHMAY24772(2-1), and from *Helminthosporium maydis* isolate 6921.

FIGS. 4A and 4B Sequence Alignment of the ITS regions from clone pCRHTUR26306(3-1) and from *Helminthosporium turcicum* isolates 26306, 6586, and 6402.

FIG. 5A and 5B Sequence Alignment of the ITS regions from *Cercospora zeae-maydis* isolate 5860 and from clones pCRCZMPOS 12(2-1) and pCRCZLAD3-1(4-3).

FIGS. 6A and 6B Sequence Alignment of the ITS regions from clone pCRHCAR16185(5-2) and from *Helminthosporium carbonum* isolates 16185 and 5870.

BRIEF DESCRIPTION OF THE SEQUENCES IN THE SEQUENCE LISTING

SEQ ID NO:1 DNA sequence of the ITS region from *Cercospora zeae-maydis* isolate #Ladder 3-1 (clone pCRCZLAD3-1(4-3)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:2 DNA sequence of the ITS region from *Cercospora zeae-maydis* isolate #POS 12 (clone pCRCZMPOS12(2-1)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:3 DNA sequence of the ITS region from *Kabatiella zeae* isolate #56351 (clone pCRKZ56351(5-1)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:4 DNA sequence of the ITS region from *Helminthosporium maydis* isolate #24772 (clone pCRHMAY24772(2-1)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:5 DNA sequence of the ITS region from *Helminthosporium maydis* isolate #11534 (clone pCRHMAY11534(4-1)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:6 DNA sequence of the ITS region from *Helminthosporium turcicum* isolate #26306 (clone pCRHTUR26306(3-1)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:7 DNA sequence of the ITS region from *Helminthosporium carbonum* isolate #16185 (clone CRHCAR16185(5-2)), comprising in the 5' to 3' direction: 3' end of small subunit rRNA gene, Internal Transcribed Spacer 1, 5.8S rRNA gene, Internal Transcribed Spacer 2, and 5' end of large subunit rRNA gene.

SEQ ID NO:8 DNA sequence of the ITS region from *Puccinia sorghi* (GenBank accession #L08734), comprising in the 5' to 3' direction: partial sequence of Internal Transcribed Spacer 1, 5.8S rRNA gene, Internal Transcribed Spacer 2, and 5' end of large subunit rRNA gene.
SEQ ID NO:9 Oligonucleotide Primer ITS 1.
SEQ ID NO:10 Oligonucleotide Primer ITS2.
SEQ ID NO:10 Oligonucleotide Primer ITS3.
SEQ ID NO:12 Oligonucleotide Primer ITS4.
SEQ ID NO:13 M13 Universal-20 Primer.
SEQ ID NO:14 Reverse Primer used in Example 2.
SEQ ID NO:15 Oligonucleotide Primer JB586.
SEQ ID NO:16 Oligonucleotide Primer JB587.
SEQ ID NO:17 Oligonucleotide Primer JB588.
SEQ ID NO:18 Oligonucleotide Primer JB589.
SEQ ID NO:19 Oligonucleotide Primer JB590.
SEQ ID NO:20 Oligonucleotide Primer JB591.
SEQ ID NO:21 Oligonucleotide Primer JB592.
SEQ ID NO:22 Oligonucleotide Primer JB593.
SEQ ID NO:23 Oligonucleotide Primer JB594.
SEQ ID NO:24 Oligonucleotide Primer JB595.
SEQ ID NO:25 Oligonucleotide Primer JB596.
SEQ ID NO:26 Oligonucleotide Primer JB597.
SEQ ID NO:27 Oligonucleotide Primer JB598.
SEQ ID NO:28 Oligonucleotide Primer JB615.
SEQ ID NO:29 Oligonucleotide Primer JB616.
SEQ ID NO:30 Oligonucleotide Primer JB617.
SEQ ID NO:31 Oligonucleotide Primer JB618.
SEQ ID NO:32 Oligonucleotide Primer JB619.
SEQ ID NO:33 Oligonucleotide Primer JB620.
SEQ ID NO:34 Oligonucleotide Primer JB621.
SEQ ID NO:35 Oligonucleotide Primer JB622.
SEQ ID NO:36 Oligonucleotide Primer JB623.
SEQ ID NO:37 Oligonucleotide Primer JB624.
SEQ ID NO:38 Oligonucleotide Primer JB625.
SEQ ID NO:39 Oligonucleotide Primer JB626.
SEQ ID NO:40 Oligonucleotide Primer JB627.
SEQ ID NO:41 Oligonucleotide Primer JB628.

DETAILED DESCRIPTION OF THE INVENTION

The present invention provides unique DNA sequences that are useful in identifying different pathotypes of plant pathogenic fungi. Particularly, the DNA sequences can be used as primers in PCR-based analysis for the identification of fungal pathotypes. The DNA sequences of the invention include the Internal Transcribed Spacer (ITS) sequences of the ribosomal RNA gene regions of particular fungal pathogens as well as primers derived from these regions that are capable of identifying the particular pathogen. These ITS DNA sequences from different pathotypes within a pathogen species or genus, which vary between the different members of the species or genus, can be used to identify those specific members.

Biomedical researchers have used PCR-based techniques for some time and with moderate success to detect pathogens in infected animal tissues. Only recently, however, has this technique been applied to detect plant pathogens. The presence of *Gaumannomyces graminis* in infected wheat has been detected using PCR of sequences specific to the pathogen mitochondrial genome (Schlesser et al., 1991; *Applied and Environ. Microbiol.* 57:553–556), and random amplified polymorphic DNA (i.e. RAPD) markers were able to distinguish numerous races of *Gremmeniella abietina*, the causal agent of scleroderris canker in conifers. More recently, primers from within DNA sequences from the ITS of the ribosomal RNA gene region of strains of Septoria, Pseudocercosporella, Fusarium, and Mycosphaerella have been identified as being useful for the identification of the fungal isolates using PCR-based techniques (WO 95/29260, herein incorporated by reference in its entirety.)

Ribosomal genes are suitable for use as molecular probe targets because of their high copy number. Despite the high conservation between mature rRNA sequences, the non-transcribed and transcribed spacer sequences are usually poorly conserved and are thus suitable as target sequences for the detection of recent evolutionary divergence. Fungal rRNA genes are organized in units, each of which encodes three mature subunits of 18S (small subunit), 5.8S, and 28S (large subunit). These subunits are separated by two Internal Transcribed Spacers, ITS1 and ITS2, of around 300 bp (White et al., 1990; In: PCR Protocols; Eds.: Innes et al.; pages 315–322). In addition, the transcriptional units are separated by non-transcribed spacer sequences (NTSs). The ITS and NTS sequences are particularly suitable for the detection of specific pathotypes of different fungal pathogens.

The DNA sequences of the invention are from the Internal Transcribed Spacer sequences of the ribosomal RNA gene region of different plant pathogens. The ITS DNA sequences from different pathotypes within a pathogen species or genus vary among the different members of the species or genus. Once having determined the ITS sequences of a pathogen, these sequences can be aligned with other ITS sequences. In this manner, primers can be derived from the ITS sequences. That is, primers can be designed based on regions within the ITS sequences that contain the greatest differences in sequence among the fungal pathotypes. These sequences and primers based on these sequences can be used to identify specific pathogens.

Particular DNA sequences of interest include ITS1 and ITS2 DNA sequences from *Helminthosporium carbonum*, *Helminthosporium turcicum*, *Helminthosporium maydis*, *Cercospora zeae-maydis*, *Kabatiella zeae* and *Puccinia sorghi*. Examples of such ITS DNA sequences are disclosed in SEQ ID Nos: 1–8. However, isolates of these organisms other than the isolates described herein may have minor sequence variations in their ITS regions. The present invention is intended to encompass the ITS DNA sequences of any isolates of these fungal pathogens. Sequences of oligonucleotide primers of interest are disclosed in SEQ ID Nos: 9–41. The sequences find use in the PCR-based identification of the pathotypes of interest.

Methods for the use of the primer sequences of the invention in PCR analysis are well known in the art. For example, see U.S. Pat. Nos. 4,683,195 and 4,683,202, as well as Schlesser et al. (1991) *Applied and Environ. Microbiol.* 57:553–556. See also, Nazar et al. (1991; *Physiol. and Molec. Plant Pathol.* 39:1–11), which used PCR amplification to exploit differences in the ITS regions of *Verticillium albo-atrum* and *Verticillium dahliae* and therefore distinguish between the two species; and Johanson and Jeger (1993; *Mycol. Res.* 97:670–674), who used similar techniques to distinguish the banana pathogens *Mycosphaerella fijiensis* and *Mycospharella musicola*.

The ITS DNA sequences of the invention can be cloned from fungal pathogens by methods known in the art. In general, the methods for the isolation of DNA from fungal isolates are known. See, Raeder & Broda (1985) *Letters in Applied Microbiology* 2:17–20; Lee et al. (1990) *Fungal Genetics Newsletter* 35:23–24; and Lee and Taylor (1990) In: *PCR Protocols: A Guide to Methods and Applications*, Innes et al. (Eds.); pages 282–287.

Alternatively, the ITS sequences of interest can be determined by PCR amplification. In an exemplified embodiment, primers to amplify the entire ITS sequence were designed according to White et al. (1990; In: PCR Protocols; Eds.: Innes et al. pages 315–322), and the amplified ITS sequence was subcloned into the pCRII cloning vector. The subcloned sequence included the left hand ITS (ITS1), the right hand ITS (ITS2), as well as the centrally located 5.8S rRNA gene. This was undertaken for *Helminthosporium carbonum, Helminthosporium turcicum, Helminthosporium maydis, Cercospora zeae-maydis* , and *Kabatiella zeae*.

Figure 3B:
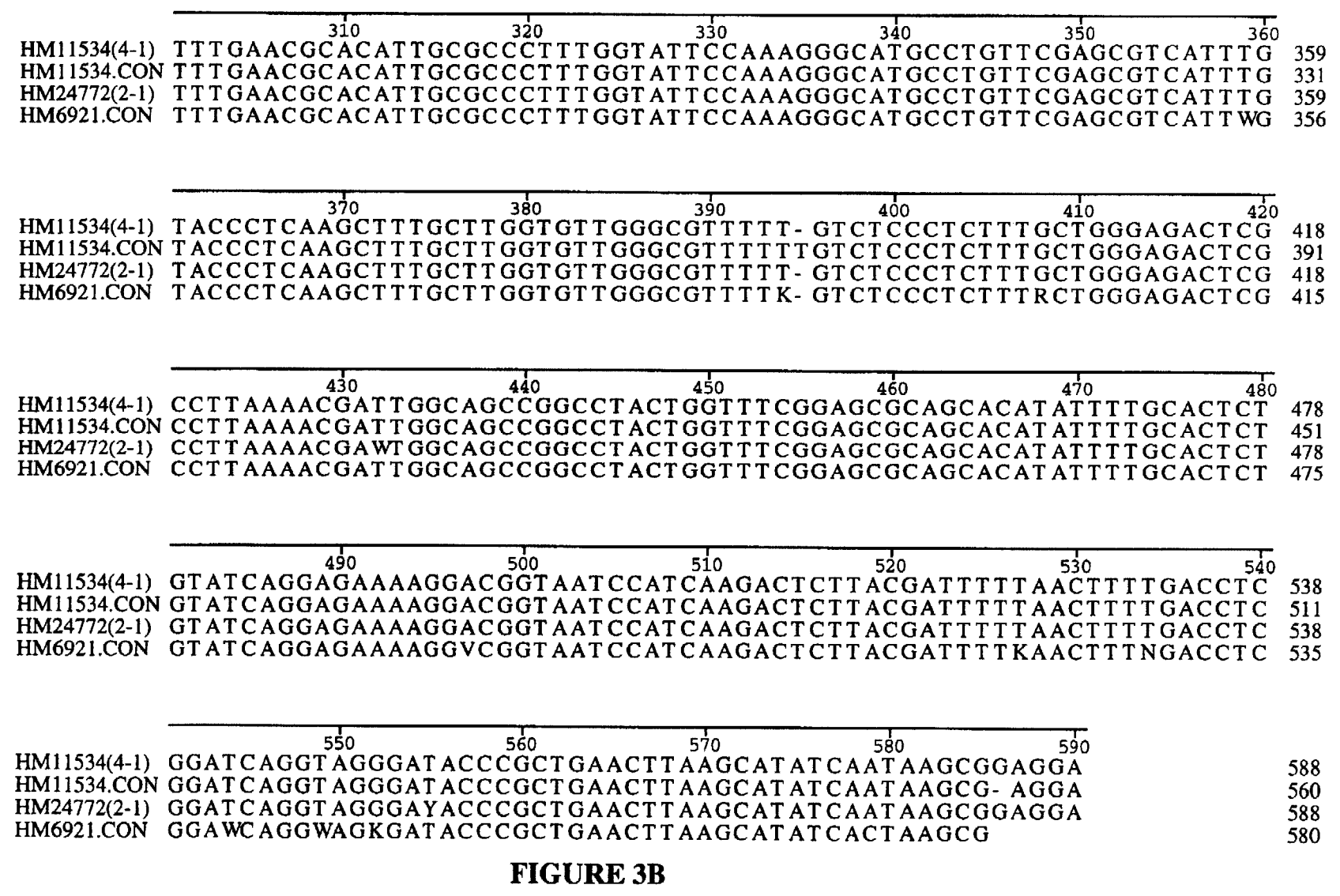
Figure 5A:
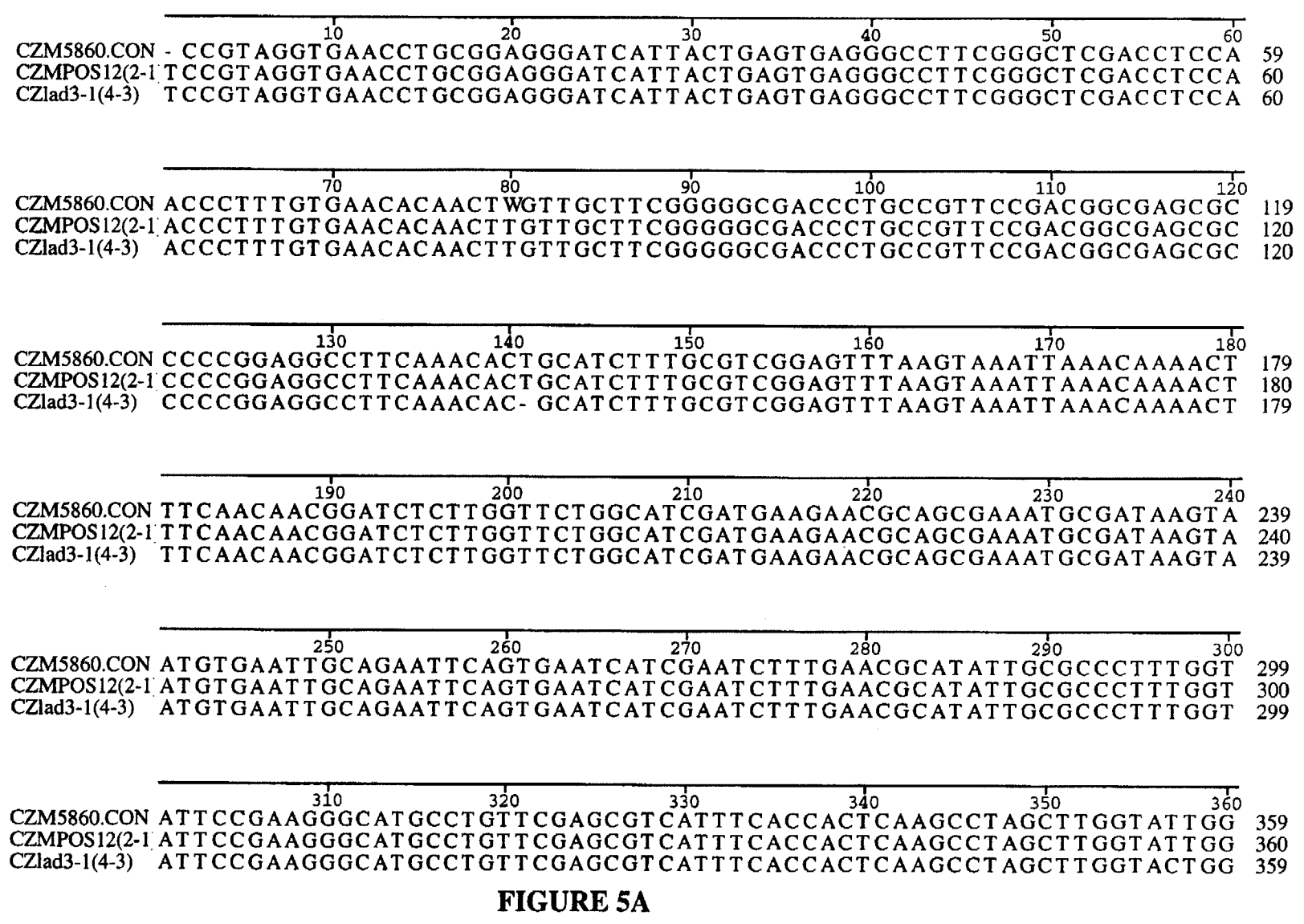

The ITS sequences were determined and the sequences were compared within each pathogen group to locate divergences that might be useful to test in PCR to distinguish the different species and/or strains. The ITS DNA sequences that were determined are shown in SEQ ID Nos: 1–7 as well as in FIGS. 1–6. From the identification of divergences, numerous primers were synthesized and tested in PCR-amplification. Templates used for PCR-amplification testing were firstly purified pathogen DNA, and subsequently DNA isolated from infected host plant tissue. Thus, it was possible to identify pairs of primers that were diagnostic, i.e. that identified one particular pathogen species or strain but not another species or strain of the same pathogen.

Preferred primer combinations are able to distinguish between the different species or strains in infected host tissue, i.e. host tissue that has previously been infected with a specific pathogen species or strain. This invention provides numerous primer combinations that fulfill this criterion for different *Helminthosporium carbonum, Helminthosporium turcicum, Helminthosporium maydis, Cercospora zeae-maydis, Kabatiella zeae*, and *Puccinia sorghi*. The primers of the invention are designed based on sequence differences among the fungal ITS regions. A minimum of one base pair difference between sequences can permit design of a discriminatory primer. Primers designed to a specific fungal DNA's ITS region can be used in combination with a primer made to a conserved sequence region within the ribosomal DNA's coding region to amplify species-specific PCR fragments. In general, primers should have a theoretical melting temperature between about 60 to about 70 degree ° C. to achieve good sensitivity and should be void of significant secondary structure and 3' overlaps between primer combinations. Primers are generally at least about 5–10 nucleotide bases long.

The present invention lends itself readily to the preparation of "kits" containing the elements necessary to carry out the process. Such a kit may comprise a carrier being compartmentalized to receive in close confinement therein one or more container, such as tubes or vials. One of the containers may contain unlabeled or detectably labeled DNA primers. The labeled DNA primers may be present in lyophilized form or in an appropriate buffer as necessary. One or more containers may contain one or more enzymes or reagents to be utilized in PCR reactions. These enzymes may be present by themselves or in mixtures, in lyophilized form or in appropriate buffers.

Finally, the kit may contain all of the additional elements necessary to carry out the technique of the invention, such as buffers, extraction reagents, enzymes, pipettes, plates, nucleic acids, nucleoside triphosphates, filter paper, gel materials, transfer materials, autoradiography supplies, and the like.

The examples below show typical experimental protocols that can be used in the isolation of ITS sequences, the selection of suitable primer sequences, the testing of primers for selective and diagnostic efficacy, and the use of such primers for disease and fungal isolate detection. Such examples are provided by way of illustration and not by way of limitation.

EXAMPLES

Standard recombinant DNA and molecular cloning techniques used here are well known in the art and are described by J. Sambrook, E. F. Fritsch and T. Maniatis, *Molecular Cloning: A Laboratory manual*, Cold Spring Harbor laboratory, Cold Spring Harbor, NY (1989) and by T. J. Silhavy, M. L. Berman, and L. W. Enquist, *Experiments with Gene Fusions*, Cold Spring Harbor Laboratory, Cold Spring Harbor, NY (1984) and by Ausubel, F. M. et al., *Current Protocols in Molecular Biology*, pub. by Greene Publishing Assoc. and Wiley-Interscience (1987).

Example 1

Fungal Isolates and Genomic Fungal DNA Extraction

See Table 1 for a listing of the fungal isolates used and their source. Fungi except for *Puccina sorghi* were grown in 150 ml potato dextrose broth inoculated with mycelial fragments from PDA (Potato Dextrose Agar) cultures. Cultures were incubated on an orbital shaker at 28° C. for 7–11 days. Mycelia were pelleted by centrifugation and then ground in liquid nitrogen and total genomic DNA extracted using the protocol of Lee and Taylor (1990; In: *PCR Protocols: A Guide to Methods and Applications*; Eds.: Innes et al.; pages 282–287). Since *P. sorghi* is an obligate biotroph and could therefore not be cultured on PDA, DNA was isolated from its spores from an infected maize leaf and ground with a Kontes pestle.

TABLE 1

Source of Test Isolates

| Fungus | Isolate | Origin | Source |
|---|---|---|---|
| *Helminthosporium maydis*[1] | 6921 | Illinois | C. Naidoo[2] |
| *Helminthosporium maydis* | XXXX | Illinois | C. Naidoo |
| *Helminthosporium maydis* | 5654 | Illinois | C. Naidoo |
| *Helminthosporium maydis* | 11534 | Maryland | ATCC[3] |
| *Helminthosporium maydis* | 4709 | Indiana | C. Naidoo |
| *Helminthosporium maydis*, Race t, mating type A | 24772 | North Carolina | ATCC[3] |
| *Helminthosporium turcicum*[4] | 6810 | Iowa | C. Naidoo |
| *Helminthosporium turcicum* | 6830 | Minnesota | C. Naidoo |
| *Helminthosporium turcicum*, Race 2 | 6402 | Illinois | C. Naidoo |
| *Helminthosporium turcicum* | 6870 | Texas | C. Naidoo |
| *Helminthosporium turcicum*, Race 1 | 6586 | Illinois | C. Naidoo |
| *Helminthosporium turcicum* | 26306 | Illinois | ATCC |
| *Helminthosporium turcicum*, Race 2 | 6294 | Indiana | C. Naidoo |
| *Helminthosporium turcicum*, Race 2 | 5352 | Ohio | C. Naidoo |
| *Helminthosporium carbonum*[5] | 5870 | Illinois | C. Naidoo |
| *Helminthosporium carbonum* | 6164 | Iowa | C. Naidoo |
| *Helminthosporium carbonum* | 6330 | Nebraska | C. Naidoo |
| *Helminthosporium carbonum* | 6378 | Iowa | C. Naidoo |
| *Helminthosporium carbonum* | 16185 | Virginia | ATCC |
| *Kabatiella zeae* | 18594 | Wisconsin | ATCC |
| *Kabatiella zeae* | 5125 | Indiana | C. Naidoo |
| *Kabatiella zeae* | 56344 | Wisconsin | ATCC |
| *Kabatiella zeae* | 56351 | Michigan | ATCC |
| *Kabatiella zeae* | 6823 | Minnesota | C. Naidoo |
| *Cercospora zeae-maydis* | 5860 | Illinois | C. Naidoo |
| *Cercospora zeae-maydis* | 6939 | Ohio | C. Naidoo |
| *Cercospora zeae-maydis* | 6911 | Illinois | C. Naidoo |
| *Cercospora zeae-maydis* | 6928 | Illinois | C. Naidoo |
| *Cercospora zeae-maydis* | SKIN11 | Indiana | L. Dunkle[6] |
| *Cercospora zeae-maydis* | Ladder 3-1 | Indiana | L. Dunkle |
| *Cercospora zeae-maydis* | POS12 | Indiana | L. Dunkle |
| *Macrophomina phaseolina* | 103 | Kansas | J. Mihail[7] |
| *Macrophomina phaseolina* | 97 | St. Charles, MO | J. Mihail |
| *Aspergillus flavus* | NRRL3557 | — | G. Payne[8] |

TABLE 1-continued Source of Test Isolates

| Fungus | Isolate | Origin | Source |
|---|---|---|---|
| *Fusarium moniliforme* | 6354 | Illinois | C. Naidoo |
| *Diplodia maydis* | 5139 | Iowa | C. Naidoo |
| *Puccinia sorghi* | IL | Illinois | C. Naidoo |
| *Puccinia sorghi* | MI | Michigan | C. Naidoo |
| *Puccinia sorghi* | IL88 | Illinois | C. Naidoo |
| *Puccinia sorghi* | VA | Virginia | C. Naidoo |
| *Puccinia polyspora* | TX96 | Texas | C. Naidoo |

[1]Syn. *Bipolaris maydis*, *Drechslera maydis*
[2]Dr. Charmaine Naidoo, Ciba Seeds Research, Bloomington, Illinois USA
[3]American Type Culture Collection, Rockville, Maryland USA
[4]Syn. *Exserohilum turcicum*, *Bipolaris turcica*, *Drechslera turcica*
[5]Syn. *Drechslera zeicola*, *Bipolaris zeicola*
[6]Dr. Larry Dunkle, Purdue University, West Lafayette, Indiana USA
[7]Dr. Jeanne Mihail, University of Missouri-Columbia, Columbia, Missouri USA
[8]Dr. Gary Payne, North Carolina State University, Raleigh, North Carolina USA Example 2

Isolation of the Internal Transcribed Spacer (ITS) Regions

The approximately 600 bp internal transcribed spacer region fragments were PCR amplified from 10 ng of genomic DNA isolated from *H. turcicum* isolates 6586, 26306 and 6402, *H. maydis* isolates 6921, 11534 and 24772, *H. carbonum* isolates 5870 and 16185, *K. zeae* isolates 56351, 18594 and 5125 and *C. zeae-maydis* isolates 5860, POS12 and Ladder 3-1using 50 pmol of primers ITS1 (5' TCCGTAGGTGAACCTGCGG-3'; SEQ ID NO:9) and ITS4 (5'-TCCTCCGCTTATTGATATGC-3'; SEQ ID NO:12). PCRs were performed as described in Example 4. PCR products were purified using Promega's Wizard DNA Clean-up kit (Madison, Wis.). The DNA sequences of the ITS regions were determined by the dideoxy method using the Applied Biosystems (Foster City, Calif.) automated sequencer with the primers ITS1 (SEQ ID NO:9), ITS2 (5'-GCTGCGTTCTTCATCGATGC-3'; SEQ ID NO:10), ITS4 (SEQ ID NO:12) and the M13 universal -20 (5'-GTAAAACGACGGCCAGT-3'; SEQ ID NO:13) and Reverse (5'-AACAGCTATGACCATG-3'; SEQ ID NO:14) primers. The ITS primers ITS1, ITS2, ITS3, and ITS4 used are detailed in White et al. (1990; In: PCR Protocols; Eds.: Innes et al. pages 315–322). PCR products from amplifications using *H. turcicum* isolate 26306, *H. maydis* isolates 11534 and 24772, *Kabatiella zeae* isolate 56351, *H. carbonum* isolate 16185, and *C. zeae-maydis* isolates POS 12 and Ladder 3-1 were cloned using the Invitrogen Corporation's (San Diego, Calif.) TA Cloning Kit (part no. K2000-01) using the pCRII or PCR2.1 cloning vector.

Example 3

DNA Extraction from Maize Leaves

DNA was extracted from maize leaves by using either a modified version of the Rapid DNA Extraction protocol from the MicroProbe Corporation's (Garden Grove, Calif.) IsoQuick Nucleic Acid Extraction Kit (cat# MXT-020-100) or by a bulk leaf maceration method. The Isoquick protocol was used to extract highly purified DNA from fungal-inoculated maize leaves for assay validation purposes. Typical yields using the IsoQuick kit were 5–10 μg of total DNA from 0.2 g of leaf tissue from which approximately 100 ng of total DNA were used in each PCR assay.

The bulk leaf maceration method was used to isolate DNA from several naturally infected maize leaves from the field to optimize the leaf field sampling method for high throughput analysis. In step 2 of this method, "Muller Extraction Buffer" is used. The potential concentration ranges of the ingredients of the Muller Extraction Buffer are as follows:

0–2.0% w/v Tween-80
0–2.0M Tris-Cl, pH 6–8
0–2.0M NaCl
0–2% BSA
0–2% sodium azide
0–500 mM EDTA
0–2% w/v tartrazin However, in the preferred embodiment of the bulk leaf maceration method, the following recipe is used: 0.1% w/v Tween-80; 0.04M Tris-Cl, pH 7.7; 0.15M NaCl; 0.1% w/v BSA-Pentex fraction V; 0.01% w/v sodium azide; 200 mM EDTA. The color dye tartrazin may optionally be added as well.

Modified Rapid DNA Extraction:

Before using the kit for the first time, the entire contents of Reagent 2A (20×Dye Concentrate) were added to Reagent 2 (Extraction Matrix).

(1) Approximately 0.2 g of leaf sample were added to a 1.5 ml eppendorf tube containing 50 μl sample buffer A and 50 μl #1 lysis solution. The leaf sample was ground with a Kontes pestle.

(2) Reagent 2 (Extraction Matrix) was shaken vigorously. 350 μl of reagent 2 was added to the sample lysate.

(3) 200 μl of Reagent 3 were added (Extraction Buffer) to the sample. The sample was vortexed 20 sec.

(4) Microcentrifugation at 12,000×g for 5 min.

(5) The aqueous phase (upper layer) was transferred to a new microcentrifuge tube. This volume was typically about 200 μl.

(6) 0.1× the volume of the aqueous phase of Reagent 4 (Sodium Acetate) was transferred to the aqueous phase sample.

(7) An equal volume of isopropanol was added to the aqueous phase sample followed by vortexing.

(8) Microcentrifugation at 12,000×g for 10 min.

(9) The supernatant was discarded without disturbing the nucleic acid pellet. 0.5 ml of −20° C. 70% ethanol was added to the pellet. The tube was vortexed to mix.

(10) Microcentrifugation at 12,000×g for 5 min.

(11) The supernatant was discarded and the pellet was allowed to dry.

(12) The nucleic acid pellet was dissolved in 50 μl TE with 100 μg/ml Rnase A.

Bulk Leaf Maceration Method:

(1) Took a random sampling of an appropriate number of leaves from a population of maize plants.

(2) Placed the leaves in a Bioreba (Reinach, Switzerland) heavy duty plastic bag (cat#490100). Weighed the plant tissue, plastic bag with leaves minus the tare (weight of the plastic bag).

(3) Added an equal volume (ml) of Muller Extraction Buffer per weight (g) of leaf tissue. Macerated the tissue using a Bioreba Homex 6 homogenizer set at 70. Ground the leaves until the tissue was fibrous.

(4) Removed maceration juice (extract) from the macerated tissue/extraction buffer.

(5) Pooled the extracts from multiple bags, if used, and vortexed well. Aliquoted the extraction juice into eppendorf tubes on ice.

(6) Boiled 100 μl of the concentrated extract for 5 minutes.

(7) Placed the boiled extract on ice.

(8) Made a 1:10 dilution by adding 10 μl from the boiled, concentrated extract to 90 μl of sterile dH₂O.

(9) Stored the diluted extracts on ice until ready to use.

Although the examples set forth herein describe using leaf tissue as the source of DNA, other plant tissue such as stem and root tissue could also be used in the above DNA extraction methods.

Example 4
Polymerase Chain Reaction Amplification

Polymerase chain reactions were performed with the GeneAmp Kit from Perkin-Elmer/Cetus (Norwalk, Conn.; part no. N808-0009) using 50 mM KCl, 2.5 mM MgCl₂, 10 mM Tris-HCl, pH8.3, containing 200 μM of each dTTP, Example 6
Selection of Species-Specific Primers The ITS regions of *H. turcicum*, *H. maydis*, *H. carbonum* and *C. zeae-maydis* were aligned (FIG. 1). Separate alignments were also made for each pathogen's isolates' ITS regions (FIGS. 2–6). Oligonucleotide primers (Table 2) were synthesized according to Example 5 based on analysis of the aligned sequences. Primers were designed to the regions that contained the greatest differences in sequence among the fungal species. In addition, the published ribosomal gene-specific primers ITS1, ITS2, ITS3 and ITS4 (White et al., 1990; In: PCR Protocols; Eds.: Innes et al. pages 315–322) were synthesized for testing in combination with the primers specific for the ITS region. Primers specific to the ITS regions of the published *Puccinia sorghi* sequence (Genbank accession#L08734, SEQ ID: 8) were also synthesized.

TABLE 2

Primer Design for Fungal Detection

| Primer Template | Primer Name | Primer Sequence |
|---|---|---|
| H. turcicum | JB586 | 5'TGGCAATCAGTGCTCTGCTG 3'(SEQ ID NO: 15) |
| H. turcicum | JB595 | 5'TCCGAGGTCAAAATGTGAGAG 3'(SEQ ID NO: 24) |
| H. maydis | JB589 | 5'CCTTTTTTTTATGCAGTTGCA 3'(SEQ ID NO: 18) |
| H. maydis | JB591 | 5'CTCCTGATACAGAGTGCAAAA 3'(SEQ ID NO: 20) |
| H. maydis | JB596 | 5'GAGGTCAAAAGTTAAAAATCGTAA 3'(SEQ ID NO: 25) |
| Helmin. spp. | JB588 | 5'CACCCATGTCTTTTGCGCAC 3'(SEQ ID NO: 17) |
| Helmin. spp. | JB587 | 5'CAGTTGCAATCAGCGTCAGTA 3'(SEQ ID NO: 16) |
| H. carbonum | JB592 | 5'CTCCTGATACAAAGCGCAAAT 3'(SEQ ID NO: 21) |
| H. carbonum | JB590 | 5'CCTTTTTTTTATGCAGTTACC 3'(SEQ ID NO: 19) |
| H. carbonum | JB598 | 5'CCGAGGTCAAAAGTTAAAAATCTA 3'(SEQ ID NO: 27) |
| H. carbonum | JB597 | 5'GGCTCCAGTTTTCAATTTTTAGAT 3'(SEQ ID NO: 26) |
| K. zeae | JB616 | 5'TGTTGTTAAAACTACCTTGTTGC 3'(SEQ ID NO: 29) |
| K. zeae | JB618 | 5'GTTTCTGTCGGCAGAAGTC 3'(SEQ ID NO: 31) |
| K. zeae | JB615 | 5'TTTGGCGGGACCGCTCGG 3'(SEQ ID NO: 28) |
| K. zeae | JB617 | 5'GAGTTAAACCAAACTCTTGTTG 3'(SEQ ID NO: 30) |
| K. zeae | JB619 | 5'CGCCAGACGTTGATTGAATG 3'(SEQ ID NO: 32) |
| C. zeae-maydis | JB593 | 5'GGCCTTCGGGCTCGACCT 3'(SEQ ID NO: 22) |
| C. zeae-maydis | JB594 | 5'CGGACAGCTCAGCCGGAG 3'(SEQ ID NO: 23) |
| C. zeae-maydis | JB620 | 5'CAACCCTTTGTGAACACAAC 3'(SEQ ID NO: 33) |
| C. zeae-maydis | JB621 | 5'CGCTCCGAAGCGATTAATG 3'(SEQ ID NO: 34) |
| C. zeae-maydis | JB622 | 5'TTCAAACACTGCATCTTTGCG 3'(SEQ ID NO: 35) |
| C. zeae-maydis | JB623 | 5'AGATTTAGACGGCCGCGAC 3'(SEQ ID NO: 36) |
| C. zeae-maydis | JB626 | 5'GAGTGAGGGCCTTCGGGC 3'(SEQ ID NO: 39) |
| C. zeae-maydis | JB627 | 5'GCTTCGGGGGCGACCC 3'(SEQ ID NO: 40) |
| C. zeae-maydis | JB628 | 5'GACCGCCCGCGCTCCG 3'(SEQ ID NO: 41) |
| P. sorghi | JB624 | 5'GTAGTCTCTATCTCAACAAC 3'(SEQ ID NO: 37) |
| P. sorghi | JB625 | 5'GTAAACAACCACCTTTAATTAT 3'(SEQ ID NO: 38) |
| 18S rDNA | ITS1 | 5'TCCGTAGGTGAACCTGCGG 3'(SEQ ID NO: 9) |
| 5.8S rDNA | ITS2 | 5'GCTGCGTTCTTCATCGATGC 3'(SEQ ID NO: 10) |
| 5.8S tDNA | ITS3 | 5'GCATCGATGAAGAACGCAGC 3'(SEQ ID NO: 11) |
| 25S rDNA | ITS4 | 5'TCCTCCGCTTATTGATATGC 3'(SEQ ID NO: 12) |

Note:
Helminthosporium spp. includes *H. maydis*, *H. turcicum* and *H. carbonum*.

dATP, dCTP, and dGTP, 50 pmol each primer, 2.5 units of Taq polymerase and 10 ng of genomic DNA or 1 μl of 1:10 diluted plant extract in a final volume of 50 μl. Reactions were run for 30–40 cycles of 15 s at 94° C., 15 s at 50° C.–70° C., and 45 s at 72° C. in a Perkin-Elmer/Cetus Model 9600 thermal cycler. The products were analyzed by loading 10 μl of each PCR sample on a 1.0% agarose gel and electrophoresed.

Example 5
Synthesis and Purification of Oligonucleotides

Oligonucleotides (primers) were synthesized by either Integrated DNA Technologies (Coralville, Iowa) or Midland Certified Reagent Company (Midland, Tex.).

Example 7

Determination of Primer Specificity to Purified Fungal Genomic DNA

PCRs were performed according to Example 4 using different primer combinations (Table 3) in an attempt to amplify a single species-specific fragment. Species-specific PCR amplification products were produced from primers designed from the ITS region between the 18S and 25S ribosomal DNA subunits of each fungal strain of interest.

TABLE 3

ITS-Derived Diagnostic PCR Primers

| Source of template DNA | 5'Primer | 3'Primer | Approximate size of amplified fragment |
|---|---|---|---|
| H. turcicum | JB586 (SEQ ID NO: 15) | JB595 (SEQ ID NO: 24) | 485 bp |
| H. maydis | JB589 (SEQ ID NO: 18) | JB591 (SEQ ID NO: 20) | 346 bp |
| H. maydis | JB589 (SEQ ID NO: 18) | JB596 (SEQ ID NO: 25) | 397 bp |
| H. maydis | JB588 (SEQ ID NO: 17) | JB596 (SEQ ID NO: 25) | 463 bp |
| H. maydis | JB588 (SEQ ID NO: 17) | JB591 (SEQ ID NO: 20) | 413 bp |
| H. maydis | JB587 (SEQ ID NO: 16) | JB596 (SEQ ID NO: 25) | 331 bp |
| H. maydis | JB587 (SEQ ID NO: 16) | JB591 (SEQ ID NO: 20) | 333 bp |
| H. maydis | JB588 (SEQ ID NO: 17) | JB598 (SEQ ID NO: 27) | 465 bp |
| H. maydis | JB587 (SEQ ID NO: 16) | JB598 (SEQ ID NO: 27) | 375 bp |
| H. carbonum | JB590 (SEQ ID NO: 19) | JB598 (SEQ ID NO: 27) | 398 bp |
| H. carbonum | JB590 (SEQ ID NO: 19) | JB592 (SEQ ID NO: 21) | 346 bp |
| H. carb./H. maydis | JB588 (SEQ ID NO: 17) | JB598 (SEQ ID NO: 27) | 465 bp |
| H. carb./H. maydis | JB587 (SEQ ID NO: 16) | JB598 (SEQ ID NO: 27) | 384 bp |
| K. zeae | JB616 (SEQ ID NO: 29) | JB618 (SEQ ID NO: 31) | 455 bp |
| K. zeae | JB615 (SEQ ID NO: 28) | ITS4 (SEQ ID NO: 12) | 508 bp |
| K. zeae | JB616 (SEQ ID NO: 29) | ITS4 (SEQ ID NO: 12) | 531 bp |
| K. zeae | JB617 (SEQ ID NO: 30) | ITS4 (SEQ ID NO: 12) | 443 bp |
| K. zeae | JB615 (SEQ ID NO: 28) | JB618 (SEQ ID NO: 31) | 433 bp |
| K. zeae | JB617 (SEQ ID NO: 30) | JB618 (SEQ ID NO: 31) | 366 bp |
| K. zeae | JB615 (SEQ ID NO: 28) | JB619 (SEQ ID NO: 32) | 402 bp |
| C. zeae-maydis | JB593 (SEQ ID NO: 22) | JB594 (SEQ ID NO: 23) | 380 bp |
| C. zeae-maydis | JB620 (SEQ ID NO: 33) | JB621 (SEQ ID NO: 34) | 393 bp |
| C. zeae-maydis | JB620 (SEQ ID NO: 33) | JB623 (SEQ ID NO: 36) | 420 bp |
| C. zeae-maydis | JB622 (SEQ ID NO: 35) | JB621 (SEQ ID NO: 34) | 320 bp |
| C. zeae-maydis | JB593 (SEQ ID NO: 22) | JB621 (SEQ ID NO: 34) | 415 bp |
| C. zeae-maydis | JB622 (SEQ ID NO: 35) | JB594 (SEQ ID NO: 23) | 285 bp |
| C. zeae-maydis | JB593 (SEQ ID NO: 22) | JB623 (SEQ ID NO: 36) | 442 bp |
| C. zeae-maydis | JB626 (SEQ ID NO: 39) | JB628 (SEQ ID NO: 41) | 427 bp |
| C. zeae-maydis | JB593 (SEQ ID NO: 22) | ITS4 (SEQ ID NO: 12) | 558 bp |
| P. sorghi | JB624 (SEQ ID NO: 37) | JB625 (SEQ ID NO: 38) | 409 bp |
| P. sorghi/Helm. spp. | JB587 (SEQ ID NO: 16) | ITS4 (SEQ ID NO: 12) | 434 bp |
| P. sorghi/Helm. spp. | JB588 (SEQ ID NO: 17) | ITS4 (SEQ ID NO: 12) | 517 bp |

Note:
Helminthosporium spp. includes H. maydis, H. turcicum and H. carbonum.

Example 8
Determination of Primer Specificity to Plant Tissue Infected with Fungi and Cross-Reactivity with Other Maize Fungal Pathogens Total genomic DNA was isolated as described in Example 3 from healthy maize leaves and from maize leaves inoculated with either H. turcicum, H. maydis, H. carbonum, K. zeae, C. zeae-maydis or P. sorghi. PCRs were performed as described in Example 4 testing the primer combinations listed in Example 7 against DNA from the maize leaves. Purified fungal genomic DNAs were obtained as described in Example 1 and PCR assayed as described in Example 4 using the species-specific primers. Other fungal DNA species and isolates were tested for the species-specific primers' ability to cross-react with them.

The H. turcicum-specific primers JB586 (SEQ ID NO:15) and JB595 (SEQ ID NO:24) amplified a 485 bp fragment from DNA from all of the isolates of H. turcicum listed in Table 1 and from H. turcicum-infected maize leaf tissue. The primer set did not amplify a diagnostic fragment from healthy maize leaf tissue nor from purified genomic DNA from H. maydis, H. carbonum, K. zeae, C. zeae-maydis and P. sorghi. The primers also did not amplify a diagnostic fragment from purified genomic DNA isolated from the common maize pathogens F. monililforme, M. phaseolina, A. flavus nor D. maydis.

Similar diagnostic results were obtained with the H. maydis -specific primers JB589 (SEQ ID NO:18) and 3B591 (SEQ ID NO:20). The primers amplified an approximately 346 bp fragment from H. maydis -infected maize tissue, as well as from purified genomic DNA isolated from all of the H. maydis isolates listed in Table 1. The primer combination JB589 and JB591 did not amplify any fragments from healthy maize tissue, nor from DNA from any of the following maize pathogens: H. turcicum, H. carbonum, K. zeae, C. zeae-maydis, P. sorghi, F. moniliforme, M. phaseolina, A. flavus and D. maydis.

The primer combination JB590 (SEQ ID NO:19) and JB598 (SEQ ID NO:27) amplified a 398 bp fragment from DNA from all of the H. carbonum isolates listed in Table 1 and from maize leaves infected with H. carbonum. The primer combination JB590 and JB598 did not amplify any fragments from healthy maize tissue, nor from DNA from any of the following maize pathogens: H. turcicum, H. maydis, K. zeae, C. zeae-maydis, P. sorghi, F. moniliforme, M. phaseolina, A. flavus and D. maydis.

The K. zeae-specific primers JB616 (SEQ ID NO:29) and JB618 (SEQ ID NO:31) amplified a 455 bp fragment from DNA from all of the isolates of K. zeae isolates listed in Table 1 and from K. zeae-infected maize leaf tissue. The primer set did not amplify a diagnostic fragment from healthy maize leaf tissue nor from purified genomic DNA from H. maydis, H. carbonum, H. turcicum, C. zeae-maydis and P. sorghi. The primers also did not amplify a diagnostic fragment from purified genomic DNA isolated from the common maize pathogens F. monililforme, M. phaseolina, A. flavus nor D. maydis.

The primer combination JB593 (SEQ ID NO:22) and JB621 (SEQ ID NO:34) amplified a 415 bp fragment from DNA from all of the C. zeae-maydis isolates listed in Table 1 and from maize leaves infected with C. zeae-maydis . The primer combination JB593 and JB621 did not amplify any fragments from healthy maize tissue, nor from DNA from any of the following maize pathogens: *H. turcicum, H. maydis, K. zeae, H. carbonum, P. sorghi, F. moniliforme, M. phaseolina, A. flavus* and *D. maydis*.

The primer combination JB624 (SEQ ID NO:37) and JB625 (SEQ ID NO:38) amplified a 409 bp fragment from all of the *P. sorghi* isolates listed in Table 1 and from *P. sorghi*-infected maize leaf tissue. The primers did not amplify from *P. polyspora, H. turcicum, H. maydis, K. zeae, H. carbonum, F. moniliforme, M. phaseolina, A. flavus* and *D. maydis*. The primers also did not amplify from healthy maize tissue.

Primers JB587 (SEQ ID NO:16) and ITS4 (SEQ ID NO:12) amplified a 434 bp fragment from *P. sorghi, H. turcicum, H. maydis* and *H. carbonum* but not from the other following maize pathogens: *K. zeae, F. moniliforme, M. phaseolina, A. flavus* and *D. maydis*. The primers also amplified a 434 bp fragment from maize infected with *P. sorghi, H. turcicum, H. maydis* and *H. carbonum* but did not amplify any fragments from healthy maize tissue.

While the present invention has been described with reference to specific embodiments thereof, it will be appreciated that numerous variations, modifications, and further embodiments are possible, and accordingly, all such variations, modifications and embodiments are to be regarded as being within the scope of the present invention.

Deposits

The following deposits were made on Nov. 6, 1996 at Agricultural Research Service, Patent Culture Collection (NRRL), Northern Regional Research Center, 1815 North University Street, Peoria, Ill. 61604, U.S.A.:

1. *E. coli* DH5α(pCRCZLAD3-1(4-3); SEQ ID NO:1): Accession No. NRRL B-21645.
2. *E. coli* DH5α(pCRCZMPOS12(2-1 ); SEQ ID NO:2): Accession No. NRRL B-21641.
3. *E. coli* DH5α(pCRKZ56351(5-1); SEQ ID NO:3): Accession No. NRRL B-21646.
4. *E. coli* DH5α(pCRHMAY24772(2-1); SEQ ID NO:4): Accession No. NRRL B-21642.
5. *E. coli* DH5α(pCRHMAY1534(4-1 ); SEQ ID NO:5): Accession No. NRRL B-21644.
6. *E. coli* DH5α(pCRHTUR26306(3-1 ); SEQ ID NO:6): Accession No. NRRL B-21643.
7. *E. coli* DH5α(pCRHCAR16185(5-2); SEQ ID NO:7): Accession No. NRRL B-21647.

---

What is claimed is:

1. An Internal Transcribed Spacer sequence selected from the group consisting of: ITS1 and ITS2 of *Helminthosporium carbonum*; ITS1 and ITS2 of *Helminthosporium turcicum*; ITS1 and ITS2 of *Helminthosporium maydis*; ITS1 and ITS2 of *Cercospora zeae-maydis*; and ITS1 and ITS2 of *Kabatiella zeae*.

2. An Internal Transcribed Spacer sequence according to claim 1, which is ITS1 of *Helminthosporium carbonum*.

3. An Internal Transcribed Spacer sequence according to claim 1, which is ITS2 of *Helminthosporium carbonum*.

4. An Internal Transcribed Spacer sequence according to claim 1, which is ITS1 of *Helminthosporium turcicum*.

5. An Internal Transcribed Spacer sequence according to claim 1, which is ITS2 of *Helminthosporium turcicum*.

6. An Internal Transcribed Spacer sequence according to claim 1, which is ITS1 of *Helminthosporium maydis*.

7. An Internal Transcribed Spacer sequence according to claim 1, which is ITS2 of *Helminthosporium maydis*.

8. An Internal Transcribed Spacer sequence according to claim 1, which is ITS1 of *Cercospora zeae-maydis*.

9. An Internal Transcribed Spacer sequence according to claim 1, which is ITS2 of *Cercospora zeae-maydis*.

10. An Internal Transcribed Spacer sequence according to claim 1, which is ITS1 of *Kabatiella zeae*.

11. An Internal Transcribed Spacer sequence according to claim 1, which is ITS2 of *Kabatiella zeae*.

12. An Internal Transcribed Spacer sequence selected from the group consisting of: nucleotides 31–175 of SEQ ID NO:1; nucleotides 333–478 of SEQ ID NO:1; nucleotides 31–176 of SEQ ID NO:2; nucleotides 334–479 of SEQ ID NO:2; nucleotides 31–217 of SEQ ID NO:3; nucleotides 374–540 of SEQ ID NO:3, nucleotides 31–200 of SEQ ID NO:4; nucleotides 359–531 of SEQ ID NO:4; nucleotides 31–200 of SEQ ID NO 5; nucleotides 359–531 of SEQ ID NO:5; nucleotides 31–199 of SEQ ID NO:6; nucleotides 357–523 of SEQ ID NO:6; nucleotides 31–202 of SEQ ID NO:7; and nucleotides 361–530 of SEQ ID NO:7.

13. An oligonucleotide primer for use in amplification-based detection of a fungal Internal Transcribed Spacer DNA sequence, wherein said primer has sequence identity with at least about 8–10 nucleotides of the sequence of claim 12.

14. An oligonucleotide primer selected from the group consisting of SEQ ID NO:15 to 41.

15. A pair of oligonucleotide primers for use in the amplification-based detection of a fungal Internal Transcribed Spacer DNA sequence, wherein at least one of said primers is the oligonucleotide primer of claim 14.

16. The pair of oligonucleotide primers according to claim 15, wherein said pair is selected from the following primer pairs;

SEQ ID NO:15 and SEQ ID NO:24;

SEQ ID NO:18 and SEQ ID NO:20;

SEQ ID NO:18 and SEQ ID NO:25;
SEQ ID NO:17 and SEQ ID NO:25;
SEQ ID NO:17 and SEQ ID NO:20;
SEQ ID NO:16 and SEQ ID NO:25;
SEQ ID NO:16 and SEQ ID NO:20;
SEQ ID NO:17 and SEQ ID NO:27;
SEQ ID NO:16 and SEQ ID NO:27;
SEQ ID NO:19 and SEQ ID NO:27;
SEQ ID NO:19 and SEQ ID NO:21;
SEQ ID NO:17 and SEQ ID NO:27;
SEQ ID NO:16 and SEQ ID NO:27;
SEQ ID NO:29 and SEQ ID NO:31;
SEQ ID NO:28 and SEQ ID NO:12;
SEQ ID NO:29 and SEQ ID NO:12;
SEQ ID NO:30 and SEQ ID NO:12;
SEQ ID NO:28 and SEQ ID NO:31;
SEQ ID NO:30 and SEQ ID NO:31;
SEQ ID NO:28 and SEQ ID NO:32;
SEQ ID NO:22 and SEQ ID NO:23;
SEQ ID NO:33 and SEQ ID NO:34;
SEQ ID NO:33 and SEQ ID NO:36;
SEQ ID NO:35 and SEQ ID NO:34;
SEQ ID NO:22 and SEQ ID NO:34;
SEQ ID NO:35 and SEQ ID NO:23;
SEQ ID NO:22 and SEQ ID NO:36;
SEQ ID NO:39 and SEQ ID NO:41;
SEQ ID NO:22 and SEQ ID NO:12;
SEQ ID NO:37 and SEQ ID NO:38;
SEQ ID NO:16 and SEQ ID NO:12; and
SEQ ID NO:17 and SEQ ID NO:12.

17. The pair of oligonucleotide primers according to claim 16, wherein said pair of primers are used to detect *H. turcicum*, and wherein said pair comprises SEQ ID NO:15 and SEQ ID NO:24.

18. The pair of oligonucleotide primers according to claim 16, wherein said pair of primers are used to detect *H. maydis*, and wherein one primer is selected from the group consisting of SEQ ID NO:16, SEQ ID NO:17, and SEQ ID NO:18 and the other primer is selected from the group consisting of SEQ ID NO:20, SEQ ID NO:25, and SEQ ID NO:27.

19. The pair of oligonucleotide primers according to claim 18, wherein said pair comprises SEQ ID NO:18 and SEQ ID NO:20.

20. The pair of oligonucleotide primers according to claim 16, wherein said pair of primers are used to detect *H. carbonum*, and wherein one primer is selected from the group consisting of SEQ ID NO:16, SEQ ID NO:17, and SEQ ID NO:19 and the other primer is selected from the group consisting of SEQ ID NO:21 and SEQ ID NO:27.

21. The pair of oligonucleotide primers according to claim 20, wherein said pair comprises SEQ ID NO:19 and SEQ ID NO:27.

22. The pair of oligonucleotide primers according to claim 16, wherein said pair of primers are used to detect *K. zeae*, and wherein one primer is selected from the group consisting of SEQ ID NO:28, SEQ ID NO:29, and SEQ ID NO:30 and the other primer is selected from the group consisting of SEQ ID NO:12, SEQ ID NO:31, and SEQ ID NO:32.

23. The pair of oligonucleotide primers according to claim 22, wherein said pair comprises SEQ ID NO:29 and SEQ ID NO:31.

24. The pair of oligonucleotide primers according to claim 16, wherein said pair of primers are used to detect *K. zeae-maydis*, and wherein one primer is selected from the group consisting of SEQ ID NO:22, SEQ ID NO:33, SEQ ID NO:35, and SEQ ID NO:39 and the other primer is selected from the group consisting of SEQ ID NO:12, SEQ ID NO:23, SEQ ID NO:34, SEQ ID NO:36, and SEQ ID NO:41.

25. The pair of oligonucleotide primers according to claim 24, wherein said pair comprises SEQ ID NO:22 and SEQ ID NO:34.

26. The pair of oligonucleotide primers according to claim 16, wherein said pair of primers are used to detect *P. sorghi*, and wherein said pair comprises SEQ ID NO:37 and SEQ ID NO:38.

27. The pair of oligonucleotide primers according to claim 16 wherein said pair of primers are used to detect *P. sorghi* and *Helminthosporium spp*, and wherein said pair comprises SEQ ID NO:16 and SEQ ID NO:12.

28. A method for the detection of a fungal pathogen, comprising the steps of:
(a) isolating DNA from a plant leaf infected with a pathogen;
(b) subjecting said DNA to polymerase chain reaction amplification using at least one primer according to claim 14, and
(c) detecting said fungal pathogen by visualizing the product or products of said polymerase chain reaction amplification.

29. The method of claim 28, wherein said fungal pathogen is selected from the group consisting of: *Helminthosporium carbonum*, *Helminthosporium turcicum*, *Helminthosporium maydis*, *Cercospora zeae-maydis*, *Kabatiella zeae*, and *Puccinia sorghi*.

30. A method for the detection of a fungal pathogen, comprising the steps of:
(a) isolating DNA from a plant leaf infected with a pathogen;
(b) amplifying a part of the Internal Transcribed Spacer sequence of said pathogen using said DNA as a template in a polymerase chain reaction with a pair of primers according to claim 16, and
(c) detecting said fungal pathogen by visualizing the amplified part of the Internal Transcribed Spacer sequence.

31. The method of claim 30, wherein said fungal pathogen is selected from the group consisting of: *Helminthosporium carbonum*, *Helminthosporium turcicum*, *Helminthosporium maydis*, *Cercospora zeae-maydis*, *Kabatiella zeae*, and *Puccinia sorghi*.

32. A diagnostic kit used in detecting a fungal pathogen, comprising the primer of claim 13.

33. A diagnostic kit used in detecting a fungal pathogen, comprising the primer of claim 14.

34. A diagnostic kit used in detecting a fungal pathogen, comprising the pair of primers of claim 15.

35. An oligonucleotide primer for use in amplification-based detection of a fungal Internal Transcribed Spacer DNA sequence, wherein said primer has sequence identity with at least 10 nucleotides of a sequence selected from the group consisting of: nucleotides 31–175 of SEQ ID NO:1; nucleotides 333–478 of SEQ ID NO:1; nucleotides 31–176 of SEQ ID NO:2; nucleotides 334–479 of SEQ ID NO:2; nucleotides 31–217 of SEQ ID NO:3; nucleotides 374–540 of SEQ ID NO:3; nucleotides 31–200 of SEQ ID NO:4;

nucleotides 359–531 of SEQ ID NO:4; nucleotides 31–200 of SEQ ID NO:5; nucleotides 359–531 of SEQ ID NO:5; nucleotides 31–199 of SEQ ID NO:6, nucleotides 357–523 of SEQ ID NO:6; nucleotides 31–202 of SEQ ID NO:7; and nucleotides 361–530 of SEQ ID NO:7.

36. A method for the detection of a fungal pathogen, comprising the steps of:
   (a) isolating DNA from plant tissue infected with a pathogen;
   (b) subjecting said DNA to polymerase chain reaction amplification using an oligonucleotide primer according to claim 35; and
   (c) detecting said fungal pathogen by visualizing the product or products of said polymerase chain reaction amplification.

37. The method of claim 36, wherein said fungal pathogen is selected from the group consisting of: *Helminthosporium carbonum*, *Helminthosporium turcicum*, *Helminthosporium maydis*, *Cercospora zeae-maydis*, *Kabatiella zeae*, and *Puccinia sorghi*.

38. A diagnostic kit used in detecting a fungal pathogen, comprising the primer of claim 35.

* * * * *

SEQUENCE LISTING ( 1 ) GENERAL INFORMATION:

( i i i ) NUMBER OF SEQUENCES: 41

( 2 ) INFORMATION FOR SEQ ID NO:1:

( i ) SEQUENCE CHARACTERISTICS:
        ( A ) LENGTH: 535 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: Cercospora zeae- maydis
        ( C ) INDIVIDUAL ISOLATE: Ladder 3- 1

( v i i ) IMMEDIATE SOURCE:
        ( B ) CLONE: pCRCZLAD3-1(4-3)

( i x ) FEATURE:
        ( A ) NAME/KEY: misc_RNA
        ( B ) LOCATION: 1..30
        ( D ) OTHER INFORMATION: /note= "3'end of small subunit rRNA gene"

( i x ) FEATURE:
        ( A ) NAME/KEY: misc_feature
        ( B ) LOCATION: 31..175
        ( D ) OTHER INFORMATION: /note= "ITS 1"

( i x ) FEATURE:
        ( A ) NAME/KEY: misc_RNA
        ( B ) LOCATION: 176..332
        ( D ) OTHER INFORMATION: /note= "5.8S rRNA gene"

( i x ) FEATURE:
        ( A ) NAME/KEY: misc_feature
        ( B ) LOCATION: 333..478
        ( D ) OTHER INFORMATION: /note= "ITS 2"

( i x ) FEATURE:
        ( A ) NAME/KEY: misc_RNA
        ( B ) LOCATION: 479..535

-continued (D) OTHER INFORMATION: /note= "5' end of large subunit rRNA gene"

(xi) SEQUENCE DESCRIPTION: SEQ ID NO:1:

```
TCCGTAGGTG AACCTGCGGA GGGATCATTA CTGAGTGAGG GCCTTCGGGC TCGACCTCCA    60
ACCCTTTGTG AACACAACTT GTTGCTTCGG GGGCGACCCT GCCGTTCCGA CGGCGAGCGC   120
CCCCGGAGGC CTTCAAACAC GCATCTTTGC GTCGGAGTTT AAGTAAATTA AACAAAACTT   180
TCAACAACGG ATCTCTTGGT TCTGGCATCG ATGAAGAACG CAGCGAAATG CGATAAGTAA   240
TGTGAATTGC AGAATTCAGT GAATCATCGA ATCTTTGAAC GCATATTGCG CCCTTTGGTA   300
TTCCGAAGGG CATGCCTGTT CGAGCGTCAT TTCACCACTC AAGCCTAGCT TGGTACTGGG   360
CGCCGCGGTG TTCCGCGCGC CTTAAAGTCT CCGGCTGAGC TGTCCGTCTC TAAGCGTTGT   420
GATTTCATTA ATCGCTTCGG AGCGCGGGCG GTCGCGGCCG TTAAATCTTT CACAAGGTTG   480
ACCTCGGATC AGGTAGGGAT ACCCGCTGAA CTTAAGCATA TCAATAAGCG GAGGA        535
```

(2) INFORMATION FOR SEQ ID NO:2:

(i) SEQUENCE CHARACTERISTICS:
(A) LENGTH: 536 base pairs
(B) TYPE: nucleic acid
(C) STRANDEDNESS: single
(D) TOPOLOGY: linear (ii) MOLECULE TYPE: DNA (genomic)

(vi) ORIGINAL SOURCE:
(B) STRAIN: Cercospora zeae- maydis
(C) INDIVIDUAL ISOLATE: POS 12

(vii) IMMEDIATE SOURCE:
(B) CLONE: pCRCZMPOS12(2-1)

(ix) FEATURE:
(A) NAME/KEY: misc_RNA
(B) LOCATION: 1..30
(D) OTHER INFORMATION: /note= "3' end of small subunit rRNA gene"

(ix) FEATURE:
(A) NAME/KEY: misc_feature
(B) LOCATION: 31..176
(D) OTHER INFORMATION: /note= "ITS 1"

(ix) FEATURE:
(A) NAME/KEY: misc_RNA
(B) LOCATION: 177..333
(D) OTHER INFORMATION: /note= "5.8S rRNA gene"

(ix) FEATURE:
(A) NAME/KEY: misc_feature
(B) LOCATION: 334..479
(D) OTHER INFORMATION: /note= "ITS 2"

(ix) FEATURE:
(A) NAME/KEY: misc_RNA
(B) LOCATION: 480..536
(D) OTHER INFORMATION: /note= "5' end of large subunit rRNA gene"

(xi) SEQUENCE DESCRIPTION: SEQ ID NO:2:

```
TCCGTAGGTG AACCTGCGGA GGGATCATTA CTGAGTGAGG GCCTTCGGGC TCGACCTCCA    60
ACCCTTTGTG AACACAACTT GTTGCTTCGG GGGCGACCCT GCCGTTCCGA CGGCGAGCGC   120
CCCCGGAGGC CTTCAAACAC TGCATCTTTG CGTCGGAGTT TAAGTAAATT AAACAAAACT   180
TTCAACAACG GATCTCTTGG TTCTGGCATC GATGAAGAAC GCAGCGAAAT GCGATAAGTA   240
ATGTGAATTG CAGAATTCAG TGAATCATCG AATCTTTGAA CGCATATTGC GCCCTTTGGT   300
```

-continued

| ATTCCGAAGG | GCATGCCTGT | TCGAGCGTCA | TTTCACCACT | CAAGCCTAGC | TTGGTATTGG | 360 |
| AGCGCCGCGGT | GTTCCGCGCG | CCTTAAAGTC | TCCGGCTGAG | CTGTCCGTCT | CTAAGCGTTG | 420 |
| TGATTTCATT | AATCGCTTCG | GAGCGCGGGC | GGTCGCGGCC | GTTAAATCTT | TCACAAGGTT | 480 |
| GACCTCGGAT | CAGGTAGGGA | TACCCGCTGT | ACTTAAGCAT | ATCAATAAGC | GGAGGA | 536 |

( 2 ) INFORMATION FOR SEQ ID NO:3:

( i ) SEQUENCE CHARACTERISTICS:
        ( A ) LENGTH: 597 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: Kabatiella zeae
        ( C ) INDIVIDUAL ISOLATE: 56351

( v i i ) IMMEDIATE SOURCE:
        ( B ) CLONE: pCRKZ56351(5-1)

( i x ) FEATURE:
        ( A ) NAME/KEY: misc_RNA
        ( B ) LOCATION: 1..30
        ( D ) OTHER INFORMATION: /note= "3' end of small subunit
            rRNA gene"

( i x ) FEATURE:
        ( A ) NAME/KEY: misc_feature
        ( B ) LOCATION: 31..217
        ( D ) OTHER INFORMATION: /note= "ITS 1"

( i x ) FEATURE:
        ( A ) NAME/KEY: misc_RNA
        ( B ) LOCATION: 218..373
        ( D ) OTHER INFORMATION: /note= "5.8S rRNA gene"

( i x ) FEATURE:
        ( A ) NAME/KEY: misc_feature
        ( B ) LOCATION: 374..540
        ( D ) OTHER INFORMATION: /note= "ITS 2"

( i x ) FEATURE:
        ( A ) NAME/KEY: misc_RNA
        ( B ) LOCATION: 541..597
        ( D ) OTHER INFORMATION: /note= "5' end of large subunit
            rRNA gene"

( x i ) SEQUENCE DESCRIPTION: SEQ ID NO:3:

| TCCGTAGGTG | AACCTGCGGA | AGGATCATTA | AAGAGTAAGG | GTGCCCAGCG | CCCGACCTCC | 60 |
| AACCCTTTGT | TGTTAAAACT | ACCTTGTTGC | TTTGGCGGGA | CCGCTCGGTC | CCCGAGCCGC | 120 |
| CGGGGGGATC | CGTCCCCCAT | GGCGAGCGCC | CGCCGGAGTT | AAACCAAACT | CTTGTTGAAC | 180 |
| AAACCGGTCG | TCTGAGTTAA | AATTTGAAT | AAATCAAAAC | TTTCAACAAC | GGATCTCTTG | 240 |
| GTTCTCGCAT | CGATGAAGAA | CGCAGCGAAA | TGCGATAAGT | AATGTGAATT | GCAGAATTCA | 300 |
| GTGAATCATC | GAATCTTTGA | ACGCACATTG | CGCCCTTGG | TATTCCGAGG | GGCATGCCTG | 360 |
| TTCGAGCGTC | ATTACACCAC | TCAAGCTCTG | CTTGGTATTG | GGCGTCCGTC | CTTTCGGGGG | 420 |
| CGCGCCTCAA | ACACCTCGGC | GAGGCCTCAC | CGGCTTCAGG | CGTAGTAGAA | TTCATTCAAT | 480 |
| CAACGTCTGG | CGAAACCGGA | GGGACTTCT | GCCGACAGAA | ACCTTTTATA | TTTTCTAGGT | 540 |
| TGACCTCGGA | TCAGGTAGGG | ATACCCGCTG | AACTTAAGCA | TATCAATAAG | CGGAGGA | 597 |

( 2 ) INFORMATION FOR SEQ ID NO:4:

( i ) SEQUENCE CHARACTERISTICS:
        ( A ) LENGTH: 588 base pairs ( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( B ) STRAIN: Helminthosporium maydis
( C ) INDIVIDUAL ISOLATE: 24772

( v i i ) IMMEDIATE SOURCE:
( B ) CLONE: pCRHMAY24772(2-1)

( i x ) FEATURE:
( A ) NAME/KEY: misc_RNA
( B ) LOCATION: 1..30
( D ) OTHER INFORMATION: /note= "3' end of small subunit rRNA gene"

( i x ) FEATURE:
( A ) NAME/KEY: misc_feature
( B ) LOCATION: 31..200
( D ) OTHER INFORMATION: /note= "ITS 1"

( i x ) FEATURE:
( A ) NAME/KEY: misc_RNA
( B ) LOCATION: 201..358
( D ) OTHER INFORMATION: /note= "5.8S rRNA gene"

( i x ) FEATURE:
( A ) NAME/KEY: misc_feature
( B ) LOCATION: 359..531
( D ) OTHER INFORMATION: /note= "ITS 2"

( i x ) FEATURE:
( A ) NAME/KEY: misc_RNA
( B ) LOCATION: 532..588
( D ) OTHER INFORMATION: /note= "5' end of large subunit rRNA gene"

( x i ) SEQUENCE DESCRIPTION: SEQ ID NO:4:

```
TCCGTAGGTG AACCTGCGGA GGGATCATTA CACAACAAAA TATGAAGGCC TGGCTTTGCG    60
GCCGGCTGAA ATATTTTTTT CACCCATGTC TTTTGCGCAC TTGTTGTTTC CTGGGCGGGT   120
TCGCCCGCCA CCAGGACCAA ACCCTAAACC TTTTTTTTAT GCAGTTGCAW TCAGCGTCAG   180
TATAAACAAT GTAATTATTA CAACTTTCAA CAACGGATCT CTTGGTTCTG GCATCGATGA   240
AGAACGCAGC GAAATGCGAT ACGTAGTGTG AATTGCAGAA TTCAGTGAAT CATCGAATCT   300
TTGAACGCAC ATTGCGCCCT TTGGTATTCC AAAGGGCATG CCTGTTCGAG CGTCATTTGT   360
ACCCTCAAGC TTTGCTTGGT GTTGGGCGTT TTTGTCTCCC TCTTTGCTGG GAGACTCGCC   420
TTAAAACGAW TGGCAGCCGG CCTACTGGTT TCGGAGCGCA GCACATATTT TGCACTCTGT   480
ATCAGGAGAA AAGGACGGTA ATCCATCAAG ACTCTTACGA TTTTTAACTT TTGACCTCGG   540
ATCAGGTAGG GAYACCCGCT GAACTTAAGC ATATCAATAA GCGGAGGA                588
```

( 2 ) INFORMATION FOR SEQ ID NO:5:

( i ) SEQUENCE CHARACTERISTICS:
( A ) LENGTH: 588 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( B ) STRAIN: Helminthosporium maydis
( C ) INDIVIDUAL ISOLATE: 11534

( v i i ) IMMEDIATE SOURCE:
( B ) CLONE: pCRHMAY11534(4-1)

( i x ) FEATURE:
  ( A ) NAME/KEY: misc_RNA
  ( B ) LOCATION: 1..30
  ( D ) OTHER INFORMATION: /note= "3' end of small subunit rRNA gene"

( i x ) FEATURE:
  ( A ) NAME/KEY: misc_feature
  ( B ) LOCATION: 31..200
  ( D ) OTHER INFORMATION: /note= "ITS 1"

( i x ) FEATURE:
  ( A ) NAME/KEY: misc_RNA
  ( B ) LOCATION: 201..358
  ( D ) OTHER INFORMATION: /note= "5.8S rRNA gene"

( i x ) FEATURE:
  ( A ) NAME/KEY: misc_feature
  ( B ) LOCATION: 359..531
  ( D ) OTHER INFORMATION: /note= "ITS 2"

( i x ) FEATURE:
  ( A ) NAME/KEY: misc_RNA
  ( B ) LOCATION: 532..588
  ( D ) OTHER INFORMATION: /note= "5' end of large subunit rRNA gene"

( x i ) SEQUENCE DESCRIPTION: SEQ ID NO:5:

```
TCCGTAGGTG AACCTGCGGA GGGATCATTA CACAACAAAA TATGAAGGCC TGGCTTTGCG      60
GCCGGCTGAA ATATTTTTTT CACCCATGTC TTTTGCGCAC TTGTTGTTTC CTGGGCGGGT     120
TCGCCCGCCA CCAGGACCAA ACCATAAACC TTTTTTTTAT GCAGTTGCAA TCAGCGTCAG     180
TATAAACAAT GTAATTATTA CAACTTTCAA CAACGGATCT CTTGGTTCTG GCATCGATGA     240
AGAACGCAGC GAAATGCGAT ACGTAGTGTG AATTGCAGAA TTCAGTGAAT CATCGAATCT     300
TTGAACGCAC ATTGCGCCCT TGGTATTCC  AAAGGGCATG CCTGTTCGAG CGTCATTTGT     360
ACCCTCAAGC TTTGCTTGGT GTTGGGCGTT TTTGTCTCCC TCTTTGCTGG GAGACTCGCC     420
TTAAAACGAT TGGCAGCCGG CCTACTGGTT TCGGAGCGCA GCACATATTT GCACTCTGT      480
ATCAGGAGAA AAGGACGGTA ATCCATCAAG ACTCTTACGA TTTTTAACTT TTGACCTCGG     540
ATCAGGTAGG GATACCCGCT GAACTTAAGC ATATCAATAA GCGGAGGA                  588
```

( 2 ) INFORMATION FOR SEQ ID NO:6:

( i ) SEQUENCE CHARACTERISTICS:
  ( A ) LENGTH: 580 base pairs
  ( B ) TYPE: nucleic acid
  ( C ) STRANDEDNESS: single
  ( D ) TOPOLOGY: linear ( i i ) MOLECULE TYPE: DNA (genomic)

( v i ) ORIGINAL SOURCE:
  ( B ) STRAIN: Helminthosporium turcicum
  ( C ) INDIVIDUAL ISOLATE: 26306

( v i i ) IMMEDIATE SOURCE:
  ( B ) CLONE: pCRHTUR26306(3-1)

( i x ) FEATURE:
  ( A ) NAME/KEY: misc_RNA
  ( B ) LOCATION: 1..30
  ( D ) OTHER INFORMATION: /note= "3' end of small subunit rRNA gene"

( i x ) FEATURE:
  ( A ) NAME/KEY: misc_feature
  ( B ) LOCATION: 31..199
  ( D ) OTHER INFORMATION: /note= "ITS 1"

( i x ) FEATURE:
  ( A ) NAME/KEY: misc_RNA

-continued ( B ) LOCATION: 200..356
( D ) OTHER INFORMATION: /note= "5.8S rRNA gene"

( i x ) FEATURE:
( A ) NAME/KEY: misc_feature
( B ) LOCATION: 357..523
( D ) OTHER INFORMATION: /note= "ITS 2"

( i x ) FEATURE:
( A ) NAME/KEY: misc_RNA
( B ) LOCATION: 524..580
( D ) OTHER INFORMATION: /note= "5'end of large subunit rRNA gene"

( x i ) SEQUENCE DESCRIPTION: SEQ ID NO:6:

```
TCCGTAGGTG AACCTGCGGA GGGATCATTA CACAAAGATA TGAAGGTAGG GTACTGGCAA    60
CAGTGCTCTG CTGAAATATT TTCACCCATG TCTTTTGCGC ACTTTTTGTT TCCTGGGCGA   120
GTTTGCTCGC CACCAGGACC CCCATATGAA CCTTTTTTGT TTTTGCACTC AGCGTCAGTA   180
CAATAATTTA ATCTATTAAA ACTTTCAACA ACGGATCTCT TGGTTCTGGC ATCGATGAAG   240
AACGCAGCGA AATGCGATAC GTAGTGTGAA TTGCAGAATT CAGTGAATCA TCGAATCTTT   300
GAACGCACAT TGCGCCCTTT GGTATTCCAA AGGGCATGCC TGTTCGAGCG TCATTTGTAC   360
CCTCAAGCTT TGCTTGGTGT TGGGCGTCTT ATTGTCTCTC CGTCTCGGGG AGACTCGCCT   420
TAAAACAATT GGCAGCCGGC CTACTGGTTT CGGAGCGCAG CACAAATTTG CGCTTGCAAT   480
CAGCCAAGGG CGGCATCCAT GAAGCCTTTT TTCTCTCACA TTTTGACCTC GGATCAGGTA   540
GGGATACCCG CTGAACTTAA GCATATCAAT AAGCGGAGGA                         580
```

( 2 ) INFORMATION FOR SEQ ID NO:7:

( i ) SEQUENCE CHARACTERISTICS:
( A ) LENGTH: 587 base pairs
( B ) TYPE: nucleic acid
( C ) STRANDEDNESS: single
( D ) TOPOLOGY: linear ( i i ) MOLECULE TYPE: DNA (genomic)

( v i ) ORIGINAL SOURCE:
( B ) STRAIN: Helminthosporium carbonum
( C ) INDIVIDUAL ISOLATE: 16185

( v i i ) IMMEDIATE SOURCE:
( B ) CLONE: pCRHCAR16185(5-2)

( i x ) FEATURE:
( A ) NAME/KEY: misc_RNA
( B ) LOCATION: 1..30
( D ) OTHER INFORMATION: /note= "3'end of small subunit rRNA gene"

( i x ) FEATURE:
( A ) NAME/KEY: misc_feature
( B ) LOCATION: 31..202
( D ) OTHER INFORMATION: /note= "ITS 1"

( i x ) FEATURE:
( A ) NAME/KEY: misc_RNA
( B ) LOCATION: 203..360
( D ) OTHER INFORMATION: /note= "5.8S rRNA gene"

( i x ) FEATURE:
( A ) NAME/KEY: misc_feature
( B ) LOCATION: 361..530
( D ) OTHER INFORMATION: /note= "ITS 2"

( i x ) FEATURE:
( A ) NAME/KEY: misc_RNA
( B ) LOCATION: 531..587
( D ) OTHER INFORMATION: /note= "5'end of large subunit rRNA gene"

( x i ) SEQUENCE DESCRIPTION: SEQ ID NO:7:

| | | | | | | |
|---|---|---|---|---|---|---|
| TCCGTAGGTG | AACCTGCGGA | GGGATCATTA | CACAACAAAA | TATGAAGGCC | CTGGCTTCGC | 60 |
| GGCCGGCTGA | AATATTTTT | CACCCATGTC | TTTTGCGCAC | TTGTTGTTTC | CTGGGCGGGT | 120 |
| TTGCCCGCCA | CCAGGACCAA | ACCATAAACC | TTTTTTTTA | TGCAGTTACC | ATCAGCGTCA | 180 |
| GTAAAAACAA | TGTAATTAAT | TACAACTTTC | AACAACGGAT | CTCTTGGTTC | TGGCATCGAT | 240 |
| GAAGAACGCA | GCGAAATGCG | ATACGTAGTG | TGAATTGCAG | AATTCAGTGA | ATCATCGAAT | 300 |
| CTTTGAACGC | ACATTGCGCC | CTTTGGTATT | CCAAAGGGCA | TGCCTGTTCG | AGCGTCATTT | 360 |
| GTACCTTCAA | GCTTTGCTTG | GTGTTGGGCG | TTTTTGTCTC | CCTCTTTCTG | GGAGACTCGC | 420 |
| CTTAAAACGA | TTGGCAGCCG | GCCTACTGGT | TTCGGAGCGC | AGCACATAAT | TTGCGCTTTG | 480 |
| TATCAGGAGA | AAAGGACGGT | AATCCATCAA | GACTCTAGAT | TTTTAACTTT | TGACCTCGGA | 540 |
| TCAGGTAGGG | ATACCCGCTG | AACTTAAGCA | TATCAATAAG | CGGAGGA | | 587 |

( 2 ) INFORMATION FOR SEQ ID NO:8:

( i ) SEQUENCE CHARACTERISTICS:
        ( A ) LENGTH: 458 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( B ) STRAIN: Puccinia sorghi
        ( C ) INDIVIDUAL ISOLATE: SZZI11

( i x ) FEATURE:
        ( A ) NAME/KEY: misc_feature
        ( B ) LOCATION: 1..45
        ( D ) OTHER INFORMATION: /note= "partial ITS 1"

( i x ) FEATURE:
        ( A ) NAME/KEY: misc_RNA
        ( B ) LOCATION: 46..201
        ( D ) OTHER INFORMATION: /note= "5.8S rRNA gene"

( i x ) FEATURE:
        ( A ) NAME/KEY: misc_feature
        ( B ) LOCATION: 202..441
        ( D ) OTHER INFORMATION: /note= "ITS 2"

( i x ) FEATURE:
        ( A ) NAME/KEY: misc_RNA
        ( B ) LOCATION: 442..458
        ( D ) OTHER INFORMATION: /note= "5' end of large subunit
        rRNA gene"

( x i ) SEQUENCE DESCRIPTION: SEQ ID NO:8:

| | | | | | | |
|---|---|---|---|---|---|---|
| ACACAAGTTT | AAAAGAATGT | AAACAACCAC | CTTTAATTAT | AAAAATAACT | TTTAACAATG | 60 |
| GATCTCTAGG | CTCTCACATC | GATGAAGAAC | ACAGTGAAAT | GTGATAAGTA | ATGTGAATTG | 120 |
| CAGAATTCAG | TGAATCATCG | AATCTTTGAA | CGCATCTTGC | GCCTTTGGT | ATTCCAAAAG | 180 |
| GCACACCTGT | TGAGTGTCA | TGAAACCCTC | TCACAAAATA | AATAATTTTT | ATTATGATTT | 240 |
| TTGTGGATGT | TGAGTGCTGC | TGTGTTACAC | ATAGCTCACT | TTAAATGTAT | AAGTCATCTT | 300 |
| CTTTATATAG | CAAAAAAGAA | GAGATGGATT | GACTTGATGT | GTAATAATTT | TTTTTCATCA | 360 |
| CATTGAGGAA | AGTAGCAATA | CTTGCCATCT | TTATATTATT | TTGTTGTTGA | GATAGAGACT | 420 |
| ACTAAACAAA | CAATTTAAAA | TTTAAGACCT | CAAATCAG | | | 458 |

( 2 ) INFORMATION FOR SEQ ID NO:9:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "primer ITS1"

( x i ) SEQUENCE DESCRIPTION: SEQ ID NO:9:

TCCGTAGGTG AACCTGCGG    19

( 2 ) INFORMATION FOR SEQ ID NO:10:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer ITS2"

( x i ) SEQUENCE DESCRIPTION: SEQ ID NO:10:

GCTGCGTTCT TCATCGATGC    20

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer ITS3"

( x i ) SEQUENCE DESCRIPTION: SEQ ID NO:11:

GCATCGATGA AGAACGCAGC    20

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer ITS4"

( x i ) SEQUENCE DESCRIPTION: SEQ ID NO:12:

TCCTCCGCTT ATTGATATGC    20

( 2 ) INFORMATION FOR SEQ ID NO:13:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "M13 universal-20 primer"

( x i ) SEQUENCE DESCRIPTION: SEQ ID NO:13:

GTAAAACGAC GGCCAGT    17

( 2 ) INFORMATION FOR SEQ ID NO:14:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "Reverse primer used in Example 2"

( x i ) SEQUENCE DESCRIPTION: SEQ ID NO:14:

AACAGCTATG ACCATG      16

( 2 ) INFORMATION FOR SEQ ID NO:15:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB586"

( x i ) SEQUENCE DESCRIPTION: SEQ ID NO:15:

TGGCAATCAG TGCTCTGCTG      20

( 2 ) INFORMATION FOR SEQ ID NO:16:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB587"

( x i ) SEQUENCE DESCRIPTION: SEQ ID NO:16:

CAGTTGCAAT CAGCGTCAGT A      21

( 2 ) INFORMATION FOR SEQ ID NO:17:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB588"

( x i ) SEQUENCE DESCRIPTION: SEQ ID NO:17:

CACCCATGTC TTTTGCGCAC      20

( 2 ) INFORMATION FOR SEQ ID NO:18:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB589"

( x i ) SEQUENCE DESCRIPTION: SEQ ID NO:18:

CCTTTTTTTT ATGCAGTTGC A      21

( 2 ) INFORMATION FOR SEQ ID NO:19:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB590"

( x i ) SEQUENCE DESCRIPTION: SEQ ID NO:19:

CCTTTTTTTT TATGCAGTTA CC    22

( 2 ) INFORMATION FOR SEQ ID NO:20:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB591"

( x i ) SEQUENCE DESCRIPTION: SEQ ID NO:20:

CTCCTGATAC AGAGTGCAAA A    21

( 2 ) INFORMATION FOR SEQ ID NO:21:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB592"

( x i ) SEQUENCE DESCRIPTION: SEQ ID NO:21:

CTCCTGATAC AAAGCGCAAA T    21

( 2 ) INFORMATION FOR SEQ ID NO:22:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB593"

( x i ) SEQUENCE DESCRIPTION: SEQ ID NO:22:

GGCCTTCGGG CTCGACCT    18

( 2 ) INFORMATION FOR SEQ ID NO:23:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB594"

( x i ) SEQUENCE DESCRIPTION: SEQ ID NO:23:

CGGACAGCTC AGCCGGAG    18

( 2 ) INFORMATION FOR SEQ ID NO:24:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB595"

( x i ) SEQUENCE DESCRIPTION: SEQ ID NO:24:

TCCGAGGTCA AAATGTGAGA G      21

( 2 ) INFORMATION FOR SEQ ID NO:25:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB596"

( x i ) SEQUENCE DESCRIPTION: SEQ ID NO:25:

GAGGTCAAAA GTTAAAAATC GTAA      24

( 2 ) INFORMATION FOR SEQ ID NO:26:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB597"

( x i ) SEQUENCE DESCRIPTION: SEQ ID NO:26:

GGCTCCAGTT TTCAATTTTT AGAT      24

( 2 ) INFORMATION FOR SEQ ID NO:27:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB598"

( x i ) SEQUENCE DESCRIPTION: SEQ ID NO:27:

CCGAGGTCAA AAGTTAAAAA TCTA      24

( 2 ) INFORMATION FOR SEQ ID NO:28:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB615"

( x i ) SEQUENCE DESCRIPTION: SEQ ID NO:28:

TTTGGCGGGA CCGCTCGG      18

( 2 ) INFORMATION FOR SEQ ID NO:29:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB616"

( x i ) SEQUENCE DESCRIPTION: SEQ ID NO:29:

TGTTGTTAAA ACTACCTTGT TGC      23

( 2 ) INFORMATION FOR SEQ ID NO:30:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB617"

( x i ) SEQUENCE DESCRIPTION: SEQ ID NO:30:

GAGTTAAACC AAACTCTTGT TG      22

( 2 ) INFORMATION FOR SEQ ID NO:31:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB618"

( x i ) SEQUENCE DESCRIPTION: SEQ ID NO:31:

GTTTCTGTCG GCAGAAGTC      19

( 2 ) INFORMATION FOR SEQ ID NO:32:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB619"

( x i ) SEQUENCE DESCRIPTION: SEQ ID NO:32:

CGCCAGACGT TGATTGAATG      20

( 2 ) INFORMATION FOR SEQ ID NO:33:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "primer JB620"

( x i ) SEQUENCE DESCRIPTION: SEQ ID NO:33:

CAACCCTTTG TGAACACAAC      20

( 2 ) INFORMATION FOR SEQ ID NO:34:

( i ) SEQUENCE CHARACTERISTICS:
 ( A ) LENGTH: 19 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "primer JB621"

( x i ) SEQUENCE DESCRIPTION: SEQ ID NO:34:

CGCTCCGAAG CGATTAATG　　　　　　　　　　　　　　　　　　　　　　　　　　　　19

( 2 ) INFORMATION FOR SEQ ID NO:35:

( i ) SEQUENCE CHARACTERISTICS:
 ( A ) LENGTH: 21 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "primer JB622"

( x i ) SEQUENCE DESCRIPTION: SEQ ID NO:35:

TTCAAACACT GCATCTTTGC G　　　　　　　　　　　　　　　　　　　　　　　　　21

( 2 ) INFORMATION FOR SEQ ID NO:36:

( i ) SEQUENCE CHARACTERISTICS:
 ( A ) LENGTH: 19 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "primer JB623"

( x i ) SEQUENCE DESCRIPTION: SEQ ID NO:36:

AGATTTAGAC GGCCGCGAC　　　　　　　　　　　　　　　　　　　　　　　　　　　19

( 2 ) INFORMATION FOR SEQ ID NO:37:

( i ) SEQUENCE CHARACTERISTICS:
 ( A ) LENGTH: 20 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "primer JB624"

( x i ) SEQUENCE DESCRIPTION: SEQ ID NO:37:

GTAGTCTCTA TCTCAACAAC　　　　　　　　　　　　　　　　　　　　　　　　　　20

( 2 ) INFORMATION FOR SEQ ID NO:38:

( i ) SEQUENCE CHARACTERISTICS:
 ( A ) LENGTH: 22 base pairs
 ( B ) TYPE: nucleic acid
 ( C ) STRANDEDNESS: single
 ( D ) TOPOLOGY: linear ( i i ) MOLECULE TYPE: other nucleic acid
 ( A ) DESCRIPTION: /desc = "primer JB625"

( x i ) SEQUENCE DESCRIPTION: SEQ ID NO:38:

GTAAACAACC ACCTTTAATT AT　　　　　　　　　　　　　　　　　　　　　　　　22

( 2 ) INFORMATION FOR SEQ ID NO:39:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "primer JB626"

(xi) SEQUENCE DESCRIPTION: SEQ ID NO:39:

GAGTGAGGGC CTTCGGGC                                         18

(2) INFORMATION FOR SEQ ID NO:40:

(i) SEQUENCE CHARACTERISTICS:
  (A) LENGTH: 17 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "primer JB627"

(xi) SEQUENCE DESCRIPTION: SEQ ID NO:40:

GCTTCGGGGG GCGACCC                                          17

(2) INFORMATION FOR SEQ ID NO:41:

(i) SEQUENCE CHARACTERISTICS:
  (A) LENGTH: 16 base pairs
  (B) TYPE: nucleic acid
  (C) STRANDEDNESS: single
  (D) TOPOLOGY: linear (ii) MOLECULE TYPE: other nucleic acid
  (A) DESCRIPTION: /desc = "primer JB628"

(xi) SEQUENCE DESCRIPTION: SEQ ID NO:41:

GACCGCCCGC GCTCCG                                           16